(12) United States Patent
Zhang et al.

(10) Patent No.: US 8,883,502 B2
(45) Date of Patent: Nov. 11, 2014

(54) EXPANDABLE CELL SOURCE OF NEURONAL STEM CELL POPULATIONS AND METHODS FOR OBTAINING AND USING THEM

(75) Inventors: Kang Zhang, San Diego, CA (US); Sheng Ding, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/821,179

(22) PCT Filed: Sep. 9, 2011

(86) PCT No.: PCT/US2011/051123
§ 371 (c)(1),
(2), (4) Date: May 23, 2013

(87) PCT Pub. No.: WO2012/034101
PCT Pub. Date: Mar. 15, 2012

(65) Prior Publication Data
US 2013/0236436 A1    Sep. 12, 2013

Related U.S. Application Data

(60) Provisional application No. 61/403,137, filed on Sep. 9, 2010.

(51) Int. Cl.
*C12N 5/02*         (2006.01)
*A61K 35/30*        (2006.01)
*C12N 5/0793*       (2010.01)
*C12N 5/0797*       (2010.01)
*A61K 35/12*        (2006.01)

(52) U.S. Cl.
CPC .......... *C12N 5/0623* (2013.01); *C12N 2501/42* (2013.01); *C12N 2506/45* (2013.01); *A61K 35/30* (2013.01); *C12N 2501/235* (2013.01); *C12N 5/0619* (2013.01); *C12N 2501/15* (2013.01); *C12N 2501/70* (2013.01); *A61K 35/12* (2013.01)
USPC ............ 435/377; 435/375; 435/383; 435/384

(58) Field of Classification Search
None
See application file for complete search history.

(56) References Cited

U.S. PATENT DOCUMENTS

| 5,033,252 A | 7/1991 | Carter |
| 5,052,558 A | 10/1991 | Carter |
| 5,323,907 A | 6/1994 | Kalvelage |
| 7,211,434 B2 * | 5/2007 | Van Der Kooy et al. ..... 435/377 |

OTHER PUBLICATIONS

Kim et al. Nat. Neuronsci Oct. 4, 2009; advanced online publication.*
Mao et al. Cell 2009;136:1017-31.*
Smith et al. Develop Biol 2008;313:107-17.*
Koyanaqi et al. J Neurosci Res 2008;86:270-80.*
Smukler et al. J Cell Biol 2006;172:79-90.*
Baker, Julie C. et al., "Wnt signaling in *Xenopus* embryos inhibits Bmp4 expression and activates neural development," *Genes & Development*, 1999, 13:3149-59 (Exhibit 4).
Bakre, Manjiri Manohar et al., "Generation of Multipotential Mesendodermal Progenitors from Mouse Embryonic Stem Cells via Sustained Wnt Pathway Activation," *Journal of Biological Chemistry*, 2007, 282:31703-12 (Exhibit 5).
Barberi, Tiziano et al., "Neural subtype specification of fertilization and nuclear transfer embryonic stem cells and application in parkinsonian mice," *Nature Biotechnology*, 2003, 21:1200-7 (Exhibit 6).
Camus, Anne et al., "Absence of Nodal signaling promotes precocious neural differentiation in the mouse embryo," *Development Biology*, 2006, 295:743-55 (Exhibit 7).
Chambers, Staurt M. et al., "Highly efficient neural conversion of human ES and iPS cells by dual inhibition of SMAD signaling," *Nature Biotechnology*, 2009, 27:275-80 (Exhibit 8).
Conti, Luciano and Elena Cattaneo, "Neural stem cell systems: physiological players or in vitro entities?," *Nature Reviews Neuroscience*, 2010, 11:176-87 (Exhibit 9).
Corbell, Denis et al., "The Human AC133 Hematopoietic Stem Cell Antigen is also Expressed in Epithelial Cells and Targeted to Plasma Membrane Protrusions,"*The Journal of Biological Chemistry*, 2000, 275:5512-20 (Exhibit 10).
Elkabetz, Y. and L. Struder, "Human ESC-derived Neural Rosettes and Neural Stem Cell Progession," *Cold Spring Harbor Symposis on Quantitative Biology*, 2008, 73:377-87 (Exhibit 11).
Elkabetz, Yechiel et al., "Human ES-cell-derived neural rosettes reveal a functionally distinct early neural stem cell stage," *Genes & Development*, 2008, 22:152-65 (Exhibit 12).
Ellis, Pam et al., "SOX2, a Persistent Marker for Multipotential Neural Stem Cells Derived from Embryonic Stem Cells, the Embryo or the Adult," *Developmental Neuroscience*, 2004, 26:148-65 (Exhibit 13).
Falk, Sven et al., "Brain Area-Specific Effect of TGF-β Signaling on WNT-Dependent Neural Stem Cell Expansion," *Cell Stem Cell*, 2008, 2:472-83 (Exhibit 14).
Gammill, Laura S. and Marianne Bronner-Fraser, "Neural Crest Specification: Migrating Into Genomics," *Nature Reviews Neuroscience*, 2003, 4:795-805 (Exhibit 15).

(Continued)

*Primary Examiner* — Janice Li
(74) *Attorney, Agent, or Firm* — Adriano & Associates

(57) ABSTRACT

The invention provides methods for obtaining neural stem cells from a mammalian embryonic or inducible pluripotent stem cell population comprising culturing mammalian embryonic or inducible pluripotent stem cells in a cell culture medium having a leukemia inhibitory factor (LIF), an inhibitor of glycogen synthase kinase 3 (GSK3), and an inhibitor of transforming growth factor β (TGF-β) under suitable conditions and obtaining isolated neural stem cells therefrom.

13 Claims, 15 Drawing Sheets

(56) References Cited

OTHER PUBLICATIONS

Gerrard, Lesley et al., "Differentiation of Human Embryonic Stem Cells to Neural Lineages in Adherent Culture by Blocking Bone Morphogenic Protein Signaling," *Stem Cells*, 2005, 23:1234-41 (Exhibit 16).

Gómez-Skarmeta, José Luis et al., "The Wnt-activated *Xiro1* gene encodes a repressor that is essential for neural development and downregulates *Bmp4*," *Development*, 2001, 128:551-60 (Exhibit 17).

Harland, Richard, "Neural induction," *Current Opinion in Genetics & Development*, 2000, 10:357-62 (Exhibit 18).

Hitoshi, Seiji et al., "Notch pathway molecules are essential for the maintenance, but not the generation, or mammalian neural stem cells," *Genes & Development*, 2002, 16:846-58 (Exhibit 19).

Hitoshi, Seiji et al., "Primitive neural stem cells from the mammalian epiblast differentiate to definitive neural stem cell under the control of Notch signaling," *Genes & Development*, 2004, 18:1806-11 (Exhibit 20).

Hur, Eun-Mi and Feng-Quan Zhou, "GSK3 signalling in neural development," *Nature Reviews Neuroscience*, 2010, 11:539-51 (Exhibit 21).

Joksimovic, Milan et al., "Spatiotemporally separable *Shh* domains in the midbrain define distinct dopaminergic progenitor pools," *PNAS*, 2009, 106:19185-90 (Exhibit 22).

Kalani, M. Yashar S. et al., "Wnt-mediated self-renewal of neural stem/progenitor cells," *PNAS*, 2008, 105:16970-5 (Exhibt 23).

Kim, Woo-Yang et al., "GSK-3 is a master regulator of neural progenitor homeostasis," *Nature Neuroscience*, 2009, 12:1390-7 (Exhibit 24).

Kléber, Maurice and Lukas Sommer, "Wnt singalling and the regulation of stem cell function," *Current Opinion in Cell Biology*, 2004, 16:681-7 (Exhibit 25).

Koch, Philipp et al., "A rosette-type, self-renewing human ES cell-derived neural stem cell with potential for in vitro instruction and synaptic integration," *PNAS*, 2009, 106:3225-30 (Exhibit 26).

Lee, Jean-Pyo et al., "Neural Stem Cell Transplantation in Mouse Brain," *Current Protocols in Neuroscience*, 2008, 42:3.10.1-23 (Exhibit 27).

Li, Wenlin et al., "Generation of Rat and Human induced Pluripotent Stem Cells by Combining Genetic Reprogramming and Chemical Inhibitors," *Cell Stem Cell*, 2009, 4:16-9 (Exhibit 28).

Li, Wenlin and Sheng Ding, "Generation of Novel Rat and Human Pluripotent Stem Cells by Reprogramming and Chemical Approaches," *Methods in Molecular Biology*, 2010, 636:293-300 (Exhibit 29).

Li, Wenlin et al., "Rapid induction and long-term self-renewal of primitive neural precursors from human embryonic stem cells by small molecule inhibitors," *PNAS*, 2011, 108:8299-304 (Exhibit 30).

Lowell, Sally et al., "Notch Promotes Neural Lineage Entry by Pluripotent Embryonic Stem Cells," *PLoS Biology*, 2006, 4:e121 (Exhibit 31).

Mao, Yingwei et al., "DISC1 regulates neural progenitor proliferation via modulation of GSK3b/b-catenin singalling," *PNAS*, 2006, 103:6907-12 (Exhibit 32).

Marzesco, Anne-Marie et al., "Release of extracellular membrane particles carrying the stem cell marker prominin-1 (CD133) from neural progenitors and other epithelial cells," *Journal of Cell Science*, 2005, 118:2849-58 (Exhibit 33).

Michaelidis, Theologos M. and D. Chichung Lie, "Wnt signaling and neural stem cells: caught in the Wnt web," *Cell Tissue Res*, 2008, 331:193-210 (Exhibit 34).

Pankratz, Matthew T. et al., "Directed Neural Differentiation of Human Embryonic Stem Cells via an Obligated Primitive Anterior Stage," *Stem Cells*, 2007, 25:1511-20 (Exhibit 35).

Qian, Xuerning et al., "Timing of CNS Cell Generation: A Programmed Sequence of Neuron and Glial Cell Production from Isolated Murine Cortical Stemm Cells," *Neuron*, 2000, 28:69-80 (Exhibit 36).

Ring, David B. et al., "Selective Glycogen Synthase Kinase 3 Inhibitors Potentiate Insulin Activation of Glucose Transport and Utilization In Vitro and In Vivo," *Diabetes*, 2003, 52:588-95 (Exhibit 37).

Sato, Noboru et al., "Maintenance of pluripotency in human and mouse embryonic stem cells through activation of Wnt signaling by a pharmacological GSK-3-specific inhibitor," *Nature Medicine*, 2004, 10:55-63 (Exhibit 38).

Seiffert, Dietmar et al., "Presenilin-1 and -2 are Molecular Targets for γ-Secretase Inhibitors," *The Journal of Biological Chemistry*, 2000, 275:34086-91 (Exhibit 39).

Seri, B. et al., "Comparison and Organization of the SCZ: A Large Germinal Layer Containing Neural Stem Cells in the Adult Mammalian Brain," *Cerebral Cortex*, 2006, 16:i103-11 (Exhibit 40).

Smidt, Marten P. et al., "A homeodomain gene Ptx3 has a highly restricted brain expression in mesencephalic dopaminergic neurons," *Proc. Natl. Acad. Sci. USA*, 1997, 94:13305-10 (Exhibit 41).

Smukler, Simon R. et al., "Embryonic stem cells assume a primitive neural stem cell fate in the absence of extrinsic influences," *The Journal of Cell Biology*, 2006, 172:79-90 (Exhibit 42).

Tang, Mianzhi et al., "Interactions of Wnt/b-Catenin Singaling and Sonic Hedgehog Regulate the Neurogenesis of Ventral Midbrain Dopamine Neurons," *J. Neurosci.*, 2010, 30:9280-91 (Exhibit 43).

Tao, Wufan and Esang Lai, "Telencephalon-Restricted Expression of BF-1, a New Member of the HNF-3/*fork head* Gene Family, in the Developing Rat Brain,"*Neuron*, 1992, 8:957-66 (Exhibit 44).

Tojo, Masayoshi et al., "The ALK-5 inhibitor A-83-01 inhibits Smad signaling and epithelial-to-mesenchymal transition by transforming growth factor-β," *Cancer Sci.*, 2005, 96:791-800 (Exhibit 45).

Tropepe, Vincent et al., "Direct Neural Fate Specification from Embryonic Stem Cells: A Primitive Mammalian Neural Stem Cell Stage Acquired through a Default Mechanism,"*Neuron*, 2001, 30:65-78 (Exhibit 46).

Watabe, Tetsuro and Kohei Miyazono, "Roles of TGF-β family singaling in stem cell renewal and differentiation," *Cell Research*, 2009, 19:103-15 (Exhibit 47).

Wobus, Anna M. and Kenneth R. Boheler, "Embryonic Stem Cells: Prospects for Developmental Biology and Cell Therapy," *Physiol. Rev.*, 2005, 85:635-78 (Exhibit 48).

Yao, Shuyuan et al., "Long-Term self-renewal and directed differentiation of human embryonic stem cells in chemically defined conditions," *PNAS*, 2006, 103:6907-12 (Exhibit 49).

Yu, Junying et al., "Induced Pluripotent Stem Cell Lines Derived from Human Somatic Cells," *Science*, 2007, 318:1917-20 (Exhibit 50).

Zhang, Su-Chun, "Neural Subtype Specification from Embryonic Stem Cells," *Brain Pathology*, 2006, 16:132-42 (Exhibit 51).

* cited by examiner

EXPANDABLE CELL SOURCE OF NEURONAL STEM CELL POPULATIONS AND METHODS FOR OBTAINING AND USING THEM

This application is a 371 application of PCT application No. PCT/US2011/051123, filed Sep. 9, 2011, which claims the priority of U.S. Ser. No. 61/403,137, filed Sep. 9, 2010, the contents of all of which are hereby incorporated by reference in their entirety into the present application.

Throughout this application various publications are referenced. The disclosures of these publications in their entireties are hereby incorporated by reference into this application in order to more fully describe the state of the art to which this invention pertains.

BACKGROUND OF THE INVENTION

To realize the potential of cell-based therapy for treating injuries and degenerative diseases, renewable sources of stem/progenitor cells need to be developed. Although embryonic stem cells (ESCs) indefinitely self-renew and have the differentiation potential to become any cell type, in practice, they are inferior to lineage-restricted cells as they are prone to causing teratomas and do not repopulate host tissues in vivo. However, significant challenges also remain in terms of the isolation and long-term expansion of most tissue-specific stem/progenitor cells from adults (e.g., even for the arguably most studied hematopoietic stem cells). Consequently, differentiation of ESCs into (e.g. hESCs) renewable tissue-specific cell types is highly desirable for various biomedical applications. If achieved, cell populations could be carefully quality controlled and serve as starting materials, omitting the need to use ESCs (e.g. hESCs) that cannot be used directly. Furthermore, despite significant advances in development of various neural induction conditions for ESCs (e.g. hESCs), most differentiation protocols use poorly defined culture conditions (e.g., going through embryonic bodies (EB) formation, using undefined medium supplements such as knockout serum replacement (KSR)), and usually yield mixed populations containing neural cells at different developmental stages, or even other embryonic germ layer lineages and undifferentiated hESCs.

In response to the need, we developed methods and robust chemically defined media conditions involving specific small molecules that rapidly and uniformly convert ESC or inducible pluripotent stem cells into neural stem cells (NSCs), which importantly, enable long-term expansion of NSCs without a loss of high neurogenic propensity and regionalizable plasticity. To our knowledge, we provide the fastest and most efficient method so far to produce neural stem cells from embryonic stem cells (ESCs). In addition, NSCs differ from previously reported hESC-derived NSCs in that they represent the primitive pre-rosette neuroepithelium that has never before been expanded in vitro long-term.

SUMMARY OF THE INVENTION

The invention provides methods for obtaining neural stem cells from a mammalian embryonic or inducible pluripotent stem cell population comprising culturing mammalian embryonic or inducible pluripotent stem cells in a cell culture medium having a leukemia inhibitory factor (LIF), an inhibitor of glycogen synthase kinase 3 (GSK3), and an inhibitor of transforming growth factor β (TGF-β) under suitable conditions and obtaining isolated neural stem cells therefrom.

The invention also provides methods for growing an isolated neural stem cell (NSC) population substantially free of non-NSC, which can self-renew and stably maintain its neural precursor or progenitor characteristics for at least 8 passages comprising culturing neural stem cells in a cell culture medium having a leukemia inhibitory factor (LIF), an inhibitor of glycogen synthase kinase 3 (GSK3), and an inhibitor of transforming growth factor β (TGF-β) under suitable conditions so as to grow the isolated neural stem cell population.

The invention further provides an isolated neural stem cell (NSC) population substantially free of non-NSC which can self-renew and stably maintain its neural precursor or progenitor characteristics for at least 8 passages and having a CD marker profile comprising: Sox2, CD133, and low or undetectable levels of Oct4.

The invention also provides a defined low protein cell culture medium for maintaining neural stem cells in an undifferentiated state, the medium comprising: A basal medium, A Leukemia inhibitory factor (LIF); An inhibitor of GSK3, and An inhibitor of TGF-β, wherein the medium is essentially feeder-free, essentially xeno-free, and essentially free of growth factors.

The invention further provides a culture medium supplement comprising a combination of a Leukemia inhibitory factor (LIF), an inhibitor of GSK3, and an inhibitor of TGF-β.

DETAILED DESCRIPTION OF THE INVENTION

Definitions

Figure 1:
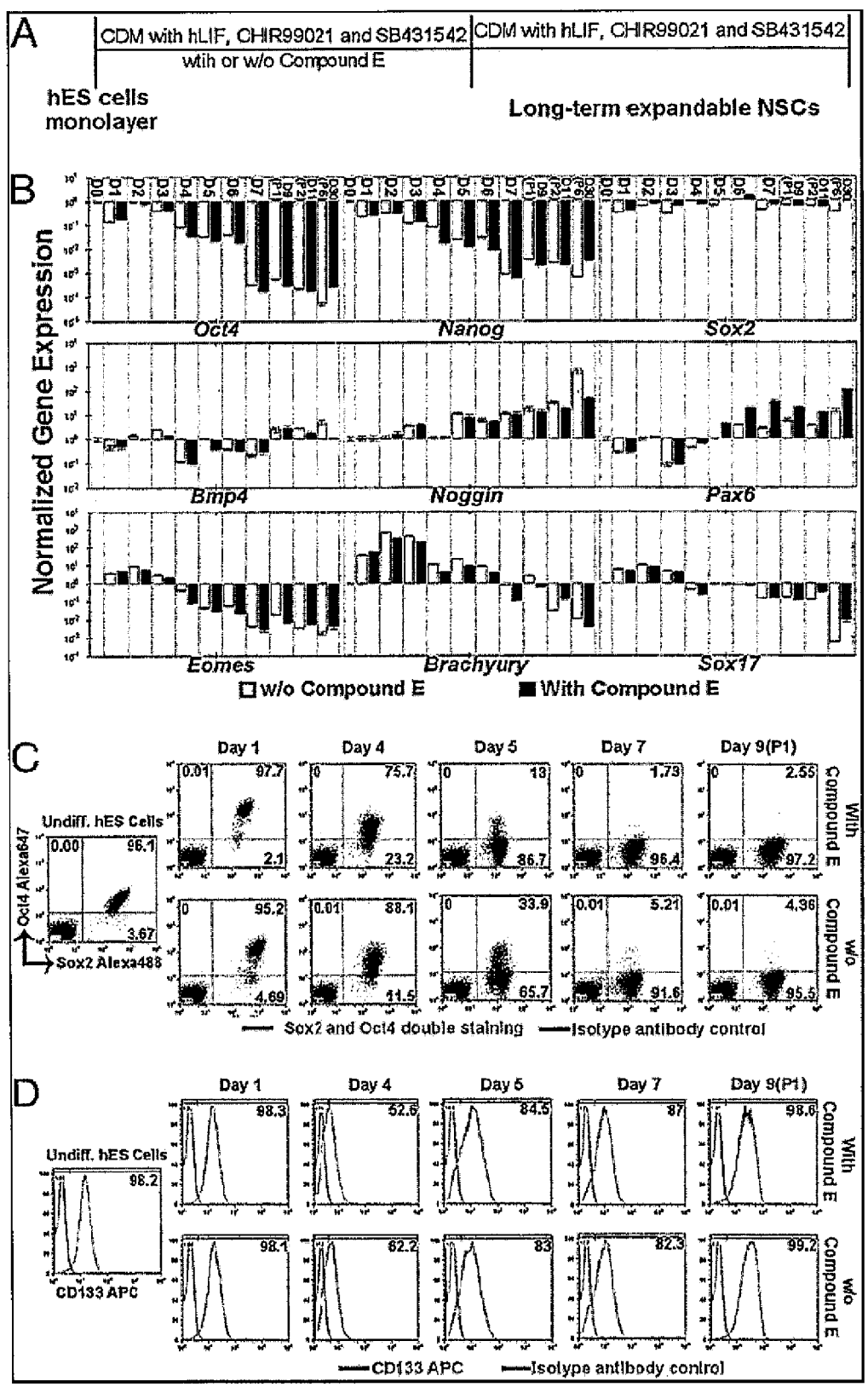
FIG. 1. Real-time PCR and flow cytometry analysis of neural induction from hESCs treated with LIF, CHIR (also referred to herein as CHIR99021), and SB431542 (with or without Compound E (also referred to herein as C-E)). (A) Schematic representation of the neural induction process. (B) The expression of Pax6, Sox2, Nanog, Oct4, BMP4, Noggin, Eomes, Brachyury, and Sox17 was analyzed by real-time PCR. (C and D) Flow cytometry analysis was used to quantify cells expressing Oct4, Sox2, or CD133 during neural induction. CDM, chemically defined medium.

All scientific and technical terms used in this application have meanings commonly used in the art unless otherwise specified. As used in this application, the following words or phrases have the meanings specified.

As used herein, the term "differentiates or differentiated" defines a stem cell that takes on a more committed ("differentiated") position within the lineage of a cell. When stem cells are fully differentiated, typically, they exit the cell cycle and hence do not divide. Fully differentiated cells generally exhibit specialized morphology and/or function and a specific set of cell markers. The "lineage" of a cell defines the heredity of the cell, i.e., which cells it came from and what cells it can give rise to. The lineage of a cell places the cell within a hereditary scheme of development and differentiation.

As used herein, a cell that differentiates into a mesodermal, ectodermal or endodermal lineage defines a cell that becomes committed to a specific mesodermal, ectodermal or endodermal lineage, respectively. Examples of cells that differentiate into a mesodermal lineage or give rise to specific mesodermal cells include, but are not limited to, cells that are adipogenic, chondrogenic, cardiogenic, dermatogenic, hematopoetic, hemangiogenic, myogenic, nephrogenic, urogenitogenic, osteogenic, pericardiogenic, or stromal. Examples of cells that differentiate into ectodermal lineage include, but are not limited to epidermal cells, neurogenic cells, and neurogliagenic cells. Examples of cells that differentiate into endodermal lineage include, but are not limited to pleurigenic cells, and hepatogenic cells, that give rise to the lining of the intestine, and cells that give rise to pancreogenic and splanchogenic cells.

As used herein, a "pluripotent stem cell" defines a less differentiated stem cell that can give rise to at least two distinct (genotypically and/or phenotypically) further differentiated progeny cells.

As used herein "isolated" defines a substance, for example a neural stem cell population, that is separated from contaminants (for example, contaminants are substances or cells that are not neural stem cells (also referred to herein as non-NSC)).

As used herein the term "transgene" or "therapeutic transgene" means DNA inserted into a stem cell encoding an amino acid sequence corresponding to a functional protein capable of exerting a therapeutic effect on cells of the CNS or having a regulatory effect on the expression of a function in the cells of the CNS. The functional molecules produced by transgenes for use in the invention include, but are not limited to, growth factors, enzymes, gangliosides, antibiotics, neurotransmitters, neurohormones, toxins, neurite promoting molecules, antimetabolites and precursors of these molecules. In particular, transgenes for insertion into donor cells include, but are not limited to, tyrosine hydroxylase, tryptophan hydroxylase, NGF, ChAT, GABA-decarboxylase, Dopa decarboxylase (AADC), enkephlin, ciliary neuronal trophic factor (CNTF), brain derived neurotrophic factor (BDNF), neurotrophin (NT)-3, NT-4, and basic fibroblast growth factor (bFGF).

As used herein, "subject" means any living organism to which the stem cells of the invention may be administered. Subjects may include, but are not limited to, humans, monkeys, cows, goats, sheep, mice, rats, cats, dogs, horses, hamsters, and any transgenic animals.

As used herein, "pharmaceutically acceptable carrier" means any material that may be combined with a composition of the invention in order to administer them to a subject in any form. For example, a carrier includes any material that will maintain the stem cells' effective activity when administered to a subject and that is non-reactive with a subject's immune system. Potential carriers may include, but are not limited to, any solvents, media, suspensions, emulsions or other excipients such as starch, milk, sugar, certain types of clay, gelatin, stearic acids, stearate salts, talcum, oils, gums, glycols, flavorings, preservatives or color additives, etc. Potential carrier forms may include sterile solutions, aerosols, liposomes, vesicles, suppositories, pills, tablets or capsules.

In order that the invention herein described may be more fully understood the following description is set forth.

Methods of the Invention

The invention provides methods for obtaining neural stem cells (NSCs (e.g. pNSCs)) from a mammalian embryonic or inducible pluripotent stem cell population comprising culturing mammalian embryonic or inducible pluripotent stem cells in a cell culture medium having a leukemia inhibitory factor (LIF), and an inhibitor of glycogen synthase kinase 3 (GSK3), and/or an inhibitor of transforming growth factor β (TGF-β) (e.g. a neural induction medium) under suitable conditions and obtaining isolated rural stem cells therefrom. Additionally, in one embodiment the cell culture medium further comprises an inhibitor of a Notch Signaling Pathway (e.g. any of NOTCH-1, -2, -3, and -4). The inhibitors may be small molecules, proteins, peptides, antibodies and nucleic acids.

Examples of GSK3 inhibitors include but are not limited to 6-(2-(4-(2,4-dichlorophenyl)-5-(4-methyl-1H-imidazol-2-yl)pyrimidin-2-ylamino)ethylamino)nicotinonitrile (also known as CHIR99021 from Cayman Chemical, IC50=7 nM), 9-Bromo-7,12-dihydro-pyrido[3',2':2,3]azepino[4,5-b]indol-6(5H)-one (or 1-azakenpaullone from Sigma-Aldrich (IC50=18 nM), (2'Z,3'E)-6-Bromoindirubin-3'-oxime (or BIO from Sigma-Aldrich; GST-3α/β inhibitor with IC50=5 nM), N-(4-Methoxybenzyl)-N'-(5-nitro-1,3-thiazol-2-yl)urea (also known as AR-A014418 from Sigma-Aldrich; GSK3 inhibitor with IC50=104 nM), Indirubin-3'-monoxime (from Enzo Life Sciences; GSK3β inhibitor with IC50=22 nM), 5-Iodo-indirubin-3'-monoxime (from Enzo Life Sciences; GSK3β inhibitor with IC50=9 nM), 9-Bromo-7,12-dihydroindolo-[3,2-d][1]benzazepin-6(5H)-one (also known as kenpaullone from Tocris Bioscience; GSK3P inhibitor with IC50=23 nM), 3-[(3-Chloro-4-hydroxyphenyl)amino]-4-(2-nitro-phenyl)-1H-pyrrole-2,5-dione (also known as SB-415286 from Sigma-Aldrich; GSK3β inhibitor with IC50=78 nM), 3-(2,4-Dichlorophenyl)-4-(1-methyl-1H-indol-3-yl)-1H-pyrrole-2,5-dione (also known as SB-216763 from Sigma-Aldrich; GSK3p inhibitor with IC50=34 nM), 2-anilino-5-phenyl-1,3,4-oxadiazole (also known as Maybridge SEW00923SC; GSK3(3 inhibitor with IC50=22 nM), (Z)-5-(2,3-Methylenedioxyphenyl)imidazolidine-2,4-dione (GSK3β inhibitor with IC50=27 nM), and Lithium salt (from Tocris Bioscience; GSK-3β Ki=2 mM).

Examples of TGF-β inhibitors include, but are not limited to, 4-[4-(1,3-benzodioxol-5-yl)-5-(2-pyridinyl)-1H-imidazol-2-yl]benzamide (also known as SB 431542 from Tocris Bioscience; potent and selective inhibitor of TGF-β type I receptor activin receptor-like kinase ALK5 with IC50=94 nM, and its relatives ALK4 and ALK7), 3-(6-Methyl-2-pyridinyl)-N-phenyl-4-(4-quinolinyl)-1H-pyrazole-1-carbothioamide (also known as A 83-01 from Tocris Bioscience; Selective inhibitor of TGF-β type I receptor ALK5 kinase, type I activin/nodal receptor ALK4 and type I nodal receptor ALK7 (IC50 values are 12, and 7.5 nM respectively), 2-(3-(6-Methylpyridine-2-yl)-1H-pyrazol-4-yl)-1,5-naphthyridine (also known as SJN 2511 from Tocris Bioscience; selective inhibitor of the TGF-β type I receptor ALK5 (IC50 values are 0.004 and 0.023 µM for ALK5 autophosphorylation and ALK5 binding, respectively), 4-[4-(2,3-Dihydro-1,4-benzodioxin-6-yl)-5-(2-pyridinyl)-1H-imidazol-2-yl]benzamide (also known as D 4476 from Tocris Bioscience; Selective inhibitor of casein kinase 1 (CK1) and TGF-β type-I receptor (ALK5) that displays >20-fold selectivity over SAPK2/p38), 4-[3-(2-Pyridinyl)-1H-pyrazol-4-yl]-quinoline (also known as LY 364947 from Tocris Bioscience; Selective inhibitor of TGF-β type-I receptor (TGF-β RI, TGFR-I, TβR-I, ALK-5) (IC50 values are 59, 400 and 1400 nM for TGR-β RI, TGF-β RII and MLK-7K respectively), 6-[2-(1,1-Dimethylethyl)-5-(6-methyl-2-pyridinyl)-1H-imidazol-4-yl]quinoxaline (also known as SB 525334 from Sigma-Aldrich; selective inhibitor of transforming growth factor-β receptor I (ALK5, TGF-βRI) with IC50=14.3 nM), 2-(5-Chloro-2-fluorophenyl)-4-[(4-pyridyl)amino]pteridine (also known as SD 208 from Tocris Bioscience; Potent, orally active ATP-competitive transforming growth factor-β receptor 1 (TGF-βRI) inhibitor with IC50=49 Nm) and 4-(6-(4-(piperazin-1-yl)phenyl)pyrazolo[1,5-a]pyrimidin-3-yl)quinoline (also known as LDN-193189 from Miltenyi Biotec).

Inhibitors of a Notch Signaling Pathway may also be a gamma inhibitor of proteolysis of Notch Intracellular Domain (NICD). Examples of inhibitors of a Notch Signaling Pathway (for example, a notch receptor) include, but are not limited to, (S,S)-2-[2-(3,5-Difluorophenyl)-acetylamino]-N-(1-methyl-2-oxo-5-phenyl-2,3-dihydro-1H-benzo[e][1,4]diazepin-3-yl)-propionamide (also known as Compound E (Santa Cruz Biotechnology) Notch signaling inhibitor with IC50=370 µM and gamma secretase inhibitor with IC50=~300 pM); N-[(3,5-Difluorophenyl)acetyl]-L-alanyl-2-phenyl]glycine-1,1-dimethylethyl ester (also known as DAPT (Tocris Bioscience) Notch signaling inhibitor and gamma secretase inhibitor); (aS)—N-[(1S)-2-[[(7S)-6,7-Dihydro-5-methyl-6-oxo-5H-dibenz[b,d]azepin-7-yl]amino]-1-methyl-2-oxoethyl]-3,5-difluoro-alpha-hydroxybenzeneacetamide (also known as LY411575 (Miltenyi Biotec) Notch signaling inhibitor and gamma secretase inhibitor); 3-((1S,3S)-3-((4-chlorophenyl)sulfonyl)-4-(2,5-difluorophenyl)cyclohexyl)propanoic acid (also known as MK0752 (Merck); Notch signaling inhibitor and gamma secretase inhibitor); 2,2-dimethyl-N-(6-oxo-6,7-dihydro-5H-dibenzo[b,d]azepin-7-yl)-N'-(2,2,3,3,3-pentafluoropropyl)malonamide (also known as RO4929097 (Roche); Notch signaling inhibitor and gamma secretase inhibitor); (S)-2-(((S)-6,8-difluoro-1,2,3,4-tetrahydronaphthalen-2-yl)amino)-N-(1-(2-methyl-1-(neopentylamino)propan-2-yl)-1H-imidazol-4-yl)pentanamide (also known as PF-03084014 (Pfizer); IC50=13.3 nM; Notch signaling inhibitor and gamma secretase inhibitor); (2S)-2-hydroxy-3-methyl-N-[(1S)-1-{[(1S)-3-methyl-2-oxo-2,3,4,5-tetrahydro-1H-3-benzazepin-1-yl]carbamoyl}ethyl]butanamide (also known as LY450139 (Eli Lilly); Notch signaling inhibitor and gamma secretase inhibitor); and (2S,3R)-3-(3,4-Difluorophenyl)-2-(4-fluorophenyl)-4-hydroxy-N-((3S)-2-oxo-5-phenyl-2,3-dihydro-1H-benzo[e][1,4]diazepin-3-yl)-butyramide (also known as γ-Secretase Inhibitor XIX (EMD Chemicals) Notch signaling inhibitor and gamma secretase inhibitor).

The neural stem cells so obtained in the methods of the invention may self-renew and stably maintain their neural precursor or progenitor characteristics over at least 8 passages without differentiating into more mature or further differentiated cells (e.g. mature neuronal cells). In one embodiment, the neural stem cells self-renew and stably maintain their neural precursor or progenitor characteristics over at least 30 passages without differentiating into more mature or further differentiated cells (e.g. mature neuronal cells).

In accordance with the practice of the invention, the cell culture medium may be free of feeder cells and/or growth factors. Also, the cell culture medium may further include a Rho-associated protein kinase (ROCK) inhibitor to enhance cell survival. Additionally, the isolated neural stem cells may be obtained within about 7 days of cell culture of the mammalian embryonic or inducible pluripotent stem cells.

Examples of rock inhibitors include, but are not limited to Y-27632 (4-[(1R)-1-aminoethyl]-N-4-pyridinyl-trans-cyclohexanecarboxamide, dihydrochloride from Cayman Chemical), or $C_{22}H_{24}N_4O_4$ (N-(2-(2-(dimethylamino)ethoxy)-4-(1H-pyrazol-4-yl)phenyl)-2,3-dihydrobenzo[b][1,4]dioxine-2-carboxamide).

Additionally, the invention provides methods for growing an isolated neural stem cell (NSC) population substantially free of non-NSC (e.g. non-NSC includes embryonic stem cells and/or inducible pluripotent stem cells) which NSC population may self-renew and stably maintain its neural precursor or progenitor characteristics for at least 8 passages (in some embodiments up to over 30 passages). In addition, the NSC population has the advantage of not being tumorigenic. In one embodiment, the method comprises culturing neural stem cells in a cell culture medium having a leukemia inhibitory factor and any one or more of an inhibitor of GSK3 and an inhibitor of TGF-β (e.g. in a neural induction medium with or without an inhibitor of Notch Signaling Pathway) under suitable conditions so as to grow and proliferate the isolated NSC. Further, the culture medium may additionally include an inhibitor of a Notch Signaling Pathway (Notch-1, -2, -3 or -4). However, in one embodiment, the cell culture medium does not contain an inhibitor of a Notch Signaling Pathway.

The invention further provides methods for differentiating (or inducing differentiation of) isolated NSC or a population thereof into any one or more of tyrosine hydroxylase (TH)-positive dopaminergic (DA) neurons that exhibit aromatic L-amino acid decarboxylase (AADC), En-1, Lmx1a, Nurr1, FoxA1, or Pitx3 comprising growing an isolated NSC population by the method described above and culturing the NSC population so grown in a neuronal differentiation medium under suitable conditions so as to produce any one or more of tyrosine hydroxylase (TH)-positive dopaminergic (DA) neurons that exhibit aromatic L-amino acid decarboxylase (AADC), En-1, Lmx1a, Nurr1, FoxA1, or Pitx3.

The invention further provides methods for differentiating (or inducing differentiation of) isolated NSC or a population thereof into any one or more of MAP2-positive neurons, GFAP-positive astrocytes, NeuN-positive neurons, GABA-expressing neurons and Double cortin (DCX) positive neuronal precursor cells comprising growing and isolated NSC population by the method described above and culturing the NSC population so grown in a neuronal differentiation medium under suitable conditions so as to produce any one or more of MAP2-positive neurons, GFAP-positive astrocytes, NeuN-positive neurons, FABA-expressing neurons and Double cortin (DCX) positive neuronal precursor cells.

The invention further provides methods for inducing the differentiation of isolated NSC or a population thereof into neural tissue. In one embodiment the method comprises culturing the isolated NSC of the invention in a neural induction medium under suitable conditions so as to induce neural tissue formation.

The invention also provides methods for regenerating or repairing neural tissue in a subject comprising introducing the isolated NSC population of the invention into the subject in a sufficient amount to regenerate or repair neural tissue.

Further, the invention provides methods for inducing the differentiation of mammalian embryonic or inducible pluripotent stem cells into an isolated NSC population of the invention. In one embodiment, the method comprises culturing mammalian (e.g., human) embryonic or inducible pluripotent stem cells in a cell culture medium containing inhibitors of GSK3, TGF-β and Notch Signaling Pathways. The method further provides the step of growing or maintaining the cells so exposed so as to become an NSC or population thereof of the invention.

The invention additionally provides compositions comprising an isolated NSC population of the invention and a biologically acceptable medium.

Depending on cell culture conditions, neural stem cells can produce colonies of differentiated cells or undifferentiated cells. The term "differentiated" is a relative term describing a cell's progression down a developmental pathway in comparison with another cell. For example the isolated NSC of the invention can give rise to any neural or neuronal cell. Examples of neuronal cells include, but are not limited to, dopaminergic neurons, motor neurons, retinal ganglion cells, photoreceptors.

Cultures of the NSC of the invention may be described as "undifferentiated" when a substantial proportion of stem cells and their derivatives in the population display morphological characteristics of undifferentiated cells and express undifferentiated markers such as SOX2, CD 133, and/or PAX6, and low or undetectable levels of OCT4. Undifferentiated NSCs are recognized by those skilled in the art.

The invention further provides methods for delivering a transgene to a subject comprising introducing an isolated NSC population of the invention containing a selected transgene into the subject, such that the transgene is expressed in the subject thereby delivering the transgene to the subject.

Additionally provided are methods for inducing the differentiation of the isolated NSC population of the invention into neuronal cells (including e.g. dopaminergic neurons, motor neurons, retinal ganglion cells, photoreceptors). In one embodiment, a method provides culturing an isolated NSC population of the invention in a suitable cell culture medium effective to induce differentiation into nerve cells. In accordance with the practice of the invention, the cell culture medium may be a neuronal differentiation medium.

Also provided are methods for treating neurological disorders. In one embodiment a method comprises administering an isolated NSC population of the invention to a subject in a sufficient amount and under suitable conditions so that the isolated NSC population exhibits functional integration (e.g. functional in vivo integration) and thereby treating the neurological disorder. As used herein, "functional integration" includes integration by the NSC population into, e.g., a local area of administration.

In accordance with the invention, examples of neurological disorders include eye diseases, Synaptic disorders, Parkinson's disease, secondary Parkinsonism, Alzheimer's disease, dystonia, schizophrenia, and Huntington's disease. Examples of eye diseases include macular degeneration and glaucoma.

The methods of the invention contemplate intracerebral administration of stem cells of the invention (e.g., wherein the isolated neural stem cells of the invention may contain a transgene) into a region of the central nervous system (CNS) having sustained defect, disease or trauma. Neural administration may involve transplantation of cells into the central nervous system or into the ventricular cavities or subdurally onto the surface of a host brain.

Conditions for successful transplantation include: 1) viability of the implant; 2) retention of the implanted cells at the site of transplantation; and 3) minimum amount of pathological reaction at the site of transplantation.

Methods for transplanting neural stem cells of the invention, into host brains are well known (e.g., Neural Grafting in the Mammalian CNS, Bjorklund and Stenevi, eds., (1985) Das, Ch. 3 pp. 23-30; Freed, Ch. 4, pp. 31-40; Stenevi et al., Ch. 5, pp. 41-50; Brundin et al., Ch. 6, pp. 51-60; David et al., Ch. 7, pp. 61-70; Seiger, Ch. 8, pp. 71-77 (1985), incorporated by reference herein. These procedures include intraparenchymal transplantation, i.e. within the host brain (as compared to outside the brain or extraparenchymal transplantation) achieved by injection or deposition of stem cells or stem cell populations of the invention within the host brain so as to be opposed to the brain parenchyma (Das, supra). The two main procedures for intraparenchymal grafting are: 1) injecting the donor cells within the host brain parenchyma or 2) preparing a cavity by surgical means to expose the host brain parenchyma and then depositing the graft into the cavity (Das, supra). Both methods provide parenchymal apposition between the graft and host brain tissue at the time of grafting, and both facilitate anatomical integration between the graft and host brain tissue. This is of importance if it is required that the graft become an integral part of the host brain and to survive for the life of the host.

Alternatively, the graft may be placed in a ventricle, e.g. a cerebral ventricle or subdurally, i.e. on the surface of the host brain where it is separated from the host brain parenchyma by the intervening pia mater or arachnoid and pia mater. For subdural grafting, the cells may be injected around the surface of the brain after making a slit in the dura. Injections into selected regions of the host brain may be made by drilling a hole and piercing the dura to permit the needle of a micro syringe to be inserted. The microsyringe is preferably mounted in a stereotaxic frame and three dimensional stereotaxic coordinates are selected for placing the needle into the desired location of the brain or spinal cord.

The donor cells may also be introduced into the putamen, nucleus basalis, hippocampus cortex, striatum or caudate regions of the brain, as well as the spinal cord.

Preferably, for passaged donor cells, cells are passaged from approximately 8 to approximately 30 passages. For grafting, the cell suspension is drawn up into the syringe and administered to anesthetized graft recipients. Multiple injections may be made using this procedure. The age of the donor tissue, i.e. the developmental stage, may affect the success of cell survival after grafting.

The cellular suspension procedure thus permits grafting of e.g. neural stem cells of the invention to any predetermined site in the brain or spinal cord, is relatively non-traumatic, allows multiple grafting simultaneously in several different sites or the same site using the same cell suspension, and permits mixtures of cells from different anatomical regions. Merely as an example, approximately $10^4$ to approximately $10^8$ cells may be introduced per graft. For transplantation into cavities, which may be preferred for spinal cord grafting, tissue may be removed from regions close to the external surface of the CNS to form a transplantation cavity, for example as described by Stenevi et al., supra, by removing bone overlying the brain and stopping bleeding with a material such a gelfoam. Suction may be used to create the cavity. The graft may then be placed in the cavity. More than one transplant may be placed in the same cavity using injection of cells or solid tissue implants. Grafting of donor cells into a traumatized brain will require different procedures, for example, the site of injury must be cleaned and bleeding stopped before attempting to graft. In addition, the donor cells should possess sufficient growth potential to fill any lesion or cavity in the host brain to prevent isolation of the graft in the pathological environment of the traumatized brain.

Compositions of the Invention

The invention also provides isolated neural stem cell (NSC) populations of the invention which are substantially free of non-NSC (excluding e.g., embryonic or inducible pluripotent stem cells), which NSC population can self-renew and stably maintain its neural precursor or progenitor characteristics in cell culture that is free of feeder cells and/or growth factors. In addition, an advantage of the NSC population is that it is non-tumorigenic.

In one embodiment, the NSC population can self-renew and stably maintain its neural precursor or progenitor characteristics for at least 8 passages, up to 30 passages, or more than 30 passages.

Additionally, the neural precursor or progenitor characteristics may include a CD marker profile comprising SOX2, and/or CD133, and low or undetectable levels of OCT4. Additionally, the NSC population may further comprise a cell surface marker profile comprising any one or more of PAX6, nestin, alkaline phosphatase (ALP), promyelocytic leukemia zinc finger (PLZF), n-CADHERIN(N-cad), ZO-1, Forse1, OTX2, Nurr1, Noggin, AP-2, En-1, Lmx1b, Pax2, Pax3, Pitx3, Nkx2.2, Nkx6.1, Dach1, and/or Hes5 or a combination thereof.

In one embodiment of the invention, the NSC population comprises SOX2, CD133, and low or undetectable levels of OCT4, and any of K5, K15, and/or SOX7, or a combination thereof.

In another embodiment of the invention, the NSC population comprises SOX2, CD133, and low or undetectable levels of OCT4, and any of alkaline phosphatase (ALP), PAX6, PLZF, N-cad, ZO-1, Forse1, Otx2, and/or Nurr1, or a combination thereof. Optionally, the NSC population may further comprise MAP2 and/or c-Fos.

In accordance with the practice of the invention the NSC population may be a mammalian NSC population. Mammals may include, but are not limited to, humans, monkeys, cows, goats, sheep, mice, rats, cats, dogs, horses, hamsters, and any transgenic animals.

The NSC population may be genetically modified e.g. with a transgene.

The NSC population may be maintained or grown in cell culture which comprises inhibitors of glycogen synthase kinase 3 (GSK3), transforming growth factor β (TGF-β) and Notch Signaling Pathways or combination thereof.

The NSC population of the invention may be homogenous. In one embodiment, the NSC population is clonal.

The invention also provides progeny cell of the NSC population of the invention. The progeny cell of the NSC population is committed to develop into a further differentiated stem cell or a more mature neural cell.

Cell Culture Media and Supplement

The invention additionally provides a defined cell culture medium for inducing and maintaining neural stem cells (e.g. pNSC). The NSC may be maintained in an undifferentiated state. In one embodiment, the medium comprises a basal medium, a leukemia inhibitory factor, an inhibitor of GSK-3, and an inhibitor of TGF-β. The media may further comprise an inhibitor of a Notch Signaling Pathway. In accordance with the invention, the medium may be essentially feeder free, essentially Xeno-free, and/or essentially free of growth factors. Examples of the basal medium include Dulbecco's modified essential medium (DMEM) or DMEM/F12.

In one embodiment, the defined cell culture media is a neuronal induction media comprising (a) basal media, e.g., Advanced DMEM/F12:Neurobasal (1:1) containing (i) 1×N2 (Gibco) which is a supplement that contains L-glutamine, 2-mercaptoethanol, nonessential amino acids, and BSA, (ii) 1×B27 (Gibco) which is a supplement that contains D-biotin, BSA, catalase, L-carnitine, corticosterone, ethanolamine, D-galactose, glutathione, insulin, linoleic acid, linolenic acid, progesterone, putrescine, sodium selenite, superoxide dismutase, T-3/albumin complex, DL-α-tocopherol, DL-α-tocopherol acetate, and transferrin, (iii) Glutmax or glutamine, BSA and hLIF and (b) supplements, e.g., (i) an inhibitor of GSK3 (e.g. CHIR99021), and (ii) an inhibitor of TGF-β (e.g. SB431542 and optionally an inhibitor of Notch Signalling Pathway (e.g., Compound E).

The neuronal induction media lacking the optional inhibitor of Notch Signalling Pathway (e.g. Compound E) may be used to maintain or propagate the neuronal stem cells (e.g. pNSCs).

The invention also provides a neuronal differentiation medium for inducing differentiation of ESCs or inhibitory postsynaptic currents (IPSCs) into neural stem cells. In one embodiment, the neuronal differentiation media comprises: (a) basal media, e.g., DMEM/F12 containing (i) 1×N2 which is a supplement that contains L-glutamine, 2-mercaptoethanol, nonessential amino acids, and BSA (bovine serum albumin) (Gibco), (ii) 1×B27 which is a supplement that contains D-biotin, BSA, catalase, L-carnitine, corticosterone, ethanolamine, D-galactose, glutathione, insulin, linoleic acid, linolenic acid, progesterone, putrescine, sodium selenite, superoxide dismutase, T-3/albumin complex, DL-α-tocopherol, DL-α-tocopherol acetate, and transferrin (Gibco), and (iii) cAMP and vitamin C and (b) differentiation supplements depending on the desired differentiated progeny (e.g., dopaminergic neuron or motor neuron).

In one embodiment, the differentiation supplement may include BDNF (brain-derived neurotrophic factor) and GDNF (glial cell-derived neurotrophic factor) for spontaneous differentiation. In another embodiment, the supplement may include SHH (Sonic Hedgehog) and FGF8b (fibroblast growth factor 8b). In a third embodiment, the supplement may include BDNF, GDNF, IGF1 (insulin-like growth factor 1), TGF-β3 (transforming growth factor beta 3) and db-cAMP (dibutyryl-cAMP). In a fourth embodiment, the supplement may include RA (retinoic acid). In a fifth embodiment, the supplement may include SHH and RA.

Further, the invention provides a cell culture medium supplement comprising a combination of a leukemia inhibitory factor, an inhibitor of GSK-3 and an inhibitor of TGF-β. Optionally, the culture medium supplement may also comprise an inhibitor of a Notch Signaling Pathway.

Kits

According to another aspect of the invention, kits are provided. Kits according to the invention include package(s) or containers comprising the compositions of the invention including stem cells, defined culture medium and cell culture medium supplement. The kit may further include an instruction letter for the treatment and/or prophylaxis of a disease, for example, a veterinary disease.

The invention provides kits for growing and maintaining the NSC population of the invention from mammalian embryonic or inducible pluripotent stem cells comprising a defined low-protein cell culture medium for maintaining neural stem cells in an undifferentiated state. In one embodiment, the kit provides a defined low-protein cell culture medium comprising a basal medium, a leukemia inhibitory factor, an inhibitor of GSK-3, and an inhibitor of TGF-β. The cell culture medium may be an induction medium or a neuronal differentiation medium. Optionally, the medium may further comprise an inhibitor of a Notch Signaling Pathway. In accordance with the invention, the medium may be essentially feeder free, essentially xeno-free, and/or essentially free of growth factors.

In another embodiment, the kit provides a cell culture medium supplement comprising a combination of a leukemia inhibitory factor, an inhibitor of GSK-3, and an inhibitor of TGF-β. Optionally, the supplement may further comprise an inhibitor of a Notch Signaling Pathway.

The phrase "package" means any vessel containing compositions (including stem cells, media, and/or media supplement) presented herein. In preferred embodiments, the package can be a box or wrapping. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment.

The kit can also contain items that are not contained within the package but are attached to the outside of the package, for example, pipettes.

Kits may optionally contain instructions for administering compositions of the present invention (including stem cells, media, and/or media supplement) to a subject having a condition in need of treatment. Kits may also comprise instructions for approved uses of compounds herein by regulatory agencies, such as the United States Food and Drug Administration. Kits may optionally contain labeling or product inserts for the present compounds. The package(s) and/or any product insert(s) may themselves be approved by regulatory agencies. The kits can include compounds in the solid phase or in a liquid phase (such as buffers provided) in a package. The kits also can include buffers for preparing solutions for conducting the methods, and pipettes for transferring liquids from one container to another.

The kit may optionally also contain one or more other compounds for use in combination therapies as described herein. In certain embodiments, the package(s) is a container for intravenous administration.

The following examples are provided to further illustrate aspects of the invention. These examples are non-limiting and should not be construed as limiting any aspect of the invention.

EXAMPLES

Example 1

Experimental Procedures

Cell and Culture Conditions.

hESCs, $H_1$ (passages 40-50), HUES9 (passages 17-30), and HUES1 (passages 20-30) were cultured in DMEM/F12, 20% knockout serum replacement, 1% glutamax, 1% nonessential amino acids, 1% penicillin/streptomycin, 0.1 mM β-mercaptoethanol, and 10 ng/mL bFGF on X-ray inactivated mouse embryonic fibroblasts. Feeder-free culture of hESCs was as described (Yao, S., Chen, S., Clark, J., Hao, E., Beattie, G. M., Hayek, A., and Ding, S. (2006)). HUES9 and HUES1 cells were passaged using Accutase (Millipore) at a dilution of 1:10. H1 cells were passaged using collagenase at a dilution of 1:6.

Figure 6:
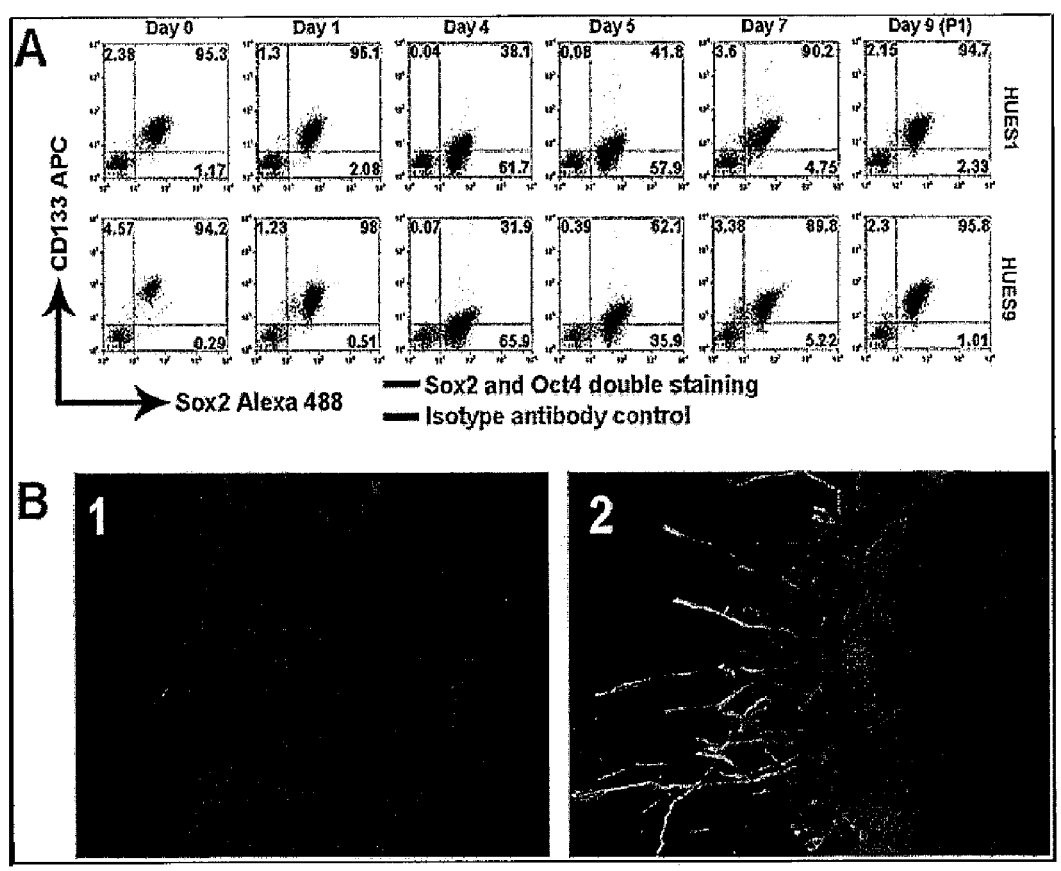
FIG. 6. (A) Flow cytometry analysis was used to quantify cells expressing Sox2 and CD133 during neural induction of hESC lines (HUES1 and HUES9) treated with CHIR, SB431542, and C-E under feeder-free condition. Although C-E can accelerate the neural induction together with CHIR and SB431542, treatment with C-E induces the differentiation of established pNSCs (passage 27) into Double cortin-positive neuronal precursors. (B1) The pNSC colony before treatment. (B2) The pNSC colony after 48-h treatment with 3 μM CHIR, 2 μM SB431542 and 0.1 μM C-E.

Neural Induction.

hESCs (HUES9 and HUES1) at about 20% confluence were treated with 3 µM CHIR99021 (Cellagentech), 2 µM SB431542 (Cellagentech), 0.1 µM Compound E (γ-Secretase Inhibitor XXI, EMD Chemicals Inc.) in neural induction media containing Advanced DMEM/F12:Neurobasal (1:1), 1×N2, 1×B27, 1% Glutmax, 5 µg/mL BSA and 10 ng/mL hLIF (Millipore), for 7 d. The culture was then split 1:3 for the next six passages using Accutase and cultured in neural induction media supplemented with 3 µM CHIR99021 and 2 µM SB431542 on X-ray inactivated MEF feeders or Matrigel-coated plates. After six passages, the cells were split 1:10 regularly. Neural induction of H1 hESCs follows the same protocol, but using 4 µM CHIR99021, 3 µM SB431542, and 0.1 µM compound E in the first 7 d, after which the cells were regularly cultured with neural induction media supplemented with 3 µM CHIR99021 and 2 µM SB431542. During the initial few passages, overnight treatment with the ROCK inhibitor (Y-27632, 5 µM, Cellagentech) was also used to enhance cell survival, but not required in following passages. In the present study, neural induction data were collected under feeder conditions except the FACS analysis of FIG. 6 performed under feeder-free condition. pNSCs were expanded on Matrigel-coated surfaces.

Neuronal Differentiation.

Spontaneous differentiation was performed in DMEM/F12, 1×N2, 1×B27, 300 ng/mL cAMP (Sigma-Aldrich) and 0.2 mM vitamin C (Sigma-Aldrich) (referred to as differentiation media) on Matrigel and poly-L-ornithine (Sigma) coated surface. The single-cell spontaneous differentiation assay was carried out by plating 200 cells/well on 6-well plates in neural induction media supplemented with 3 µM CHIR99021 and 2 µM SB431542. After 3 d, the medium was switched to differentiation medium with 10 ng/mL BDNF and 10 ng/mL GDNF for another 14 d. For dopaminergic neuron differentiation, cells were first treated with 100 ng/mL SHH (C24II) and 100 ng/mL FGF8b in differentiation media for 10 d, and then with 10 ng/mL BDNF, 10 ng/mL GDNF, 10 ng/mL IGF1, 1 ng/mL TGF-β3 and 0.5 mM db-cAMP (Sigma-Aldrich) for another 14-21 d in differentiation media. For induction of motor neurons, cells were sequentially treated with 1 µM RA (Sigma-Aldrich) in differentiation media for 7 d, then with 100 ng/nit SHH(C24II) and 0.1 µM RA for additional 7 d, and finally with 50 ng/mL SHH(C24II) and 0.1 µM RA for another 7 d. The cells were terminally differentiated in the presence of 10 ng/mL BDNF and 10 ng/mL GDNF in the differentiation media for about 7 d. All growth factors were from R&D Systems. All tissue culture products were obtained from Invitrogen except where mentioned.

Immunocytochemistry and Flow Cytometry.

For immunofluorescence assays, pNSCs were fixed in 4% paraformaldehyde for 10 min. Specifically, 4% paraformaldehyde with 0.15% picric acid was used to fix the neuronal differentiation culture. For immunostaining of GABA antigen, the cells were fixed in 4% paraformaldehyde, 0.15% picric acid and 0.02% Glutaraldehyde. The fixed cells were washed three times with PBS containing 0.1% Triton X-100 (Sigma-Aldrich) and incubated in blocking buffer, 0.1% Triton X-100 and 10% normal donkey serum (Jackson ImmunoResearch) in PBS (Invitrogen/Gibco BRL), for 30 min at room temperature. The cells were then incubated with primary antibody overnight at 4° C. in blocking buffer. The following day, cells were washed with PBS and incubated with Alexa Fluorconjugated secondary antibodies (Invitrogen, 1,000×) in PBS containing 0.1% Triton X-100 for one hour at RT. The primary antibodies were described in Table 1. Nuclei were visualized by DAPI staining (Sigma-Aldrich). Images were captured using a Nikon Eclipse TE2000-U microscope. For direct flow cytometry, cells were incubated with Alexa Fluor 647-conjugated mouse anti-Oct4, Alexa Fluor 488 conjugated mouse anti-Sox2, MAP2 and Ki-67 (BD Biosciences), APC conjugated Nestin (R&D Systems) and CD133 (Miltenyi Biotec) for 10 min at 4° C. Corresponding isotype antibodies were used as controls. For indirect flow cytometry, cells were incubated with mouse anti-Forse1 (Developmental Studies Hybridoma Bank, 1:50), rabbit anti-Pax6 (Covance, 1:2,000), rabbit anti-TH (Novus Biologics, 1:200), rabbit anti-Isl-1 (Abeam, 1:1,000) and mouse anti-NeuN (Millipore, 1:500) on ice for 1 h and washed three times. Cells were then incubated with Alexa Fluor 647 F(ab')2 fragment of goat anti-rabbit or anti-mouse IgG (Invitrogen, 1:1,000) for 30 min on ice and washed three times. Cells directly incubated with secondary antibody were used as control. BD Cytofix/Cytoperm kit (BD Biosciences) was used for fixation, permeabilization, and washing for intracellular staining. Live cells were used for cell surface marker staining and cells were washed with PBS containing 0.5% BSA and 2 mM EDTA after staining. For cell cycle analysis of propidium iodide staining, $2\times10^6$ cells were fixed with 70% ethanol overnight at −20° C. Cells were then washed twice with cold PBS, resuspended in 500 µL of propidium iodide solution (0.1% sodium citrate, pH 7.2/0.1% Triton X-100/50 µg/mL propidium iodide/200 µg/mL RNase) and incubated at 37° C. for 30 min. Flow cytometry analysis was carried out with a FACScan flow cytometer (Becton Dickinson).

TABLE 1

Antibodies used in immunocytochemistry

| Antibodies | Source | Dilution |
|---|---|---|
| Oct4 | Santa Cruz, sc-5279 | 200 |
| Sox2 | Millipore, AB5603 | 2,000 |
| Nestin | Covance, PBR-315C | 1,500 |
| Pax6 | Covance, PRB-278P | 1,500 |
| Otx2 | Millipore, AB9566 | 1,000 |
| Nurr1 | Santa Cruz/sc-990 | 200 |
| En-1 | Santa Cruz, sc-66876 | 300 |
| SSEA1 | Santa Cruz, sc-21702 | 200 |
| Forse1 | Developmental Studies Hybridoma Bank | 50 |
| PLZF | Calbiochem/op128 | 200 |
| N-cad | BD, 610920 | 200 |
| Ki-67 | BD, 556003 | 200 |
| ZO-1 | Invitrogen, 61-7300 | 200 |
| MAP2 | Abcam, AB5392-25 | 5,000 |
| GFAP | DAKO, ZO334 | 1,500 |
| TH | Millipore/AB152, AB9702 | 1,000 |
| FoxA2 | Millipore, AB4125 | 1,000 |
| Lmx1a | Millipore, AB10533 | 1,000 |
| Pitx3 | Millipore, AB5722 | 1 µg/mL |
| AADC | Millipore, AB1569 | 1,000 |
| GABA | Sigma, A2052 | 3,000 |
| ChAT | Millipore, AB144P | 1,000 |
| Isl1 | Abcam, ab20670 | 500 |
| O4 | R&D Systems, MAB1326 | 1 µg/mL |
| Peripherin | Millipore, AB1530 | 1,000 |
| α-SMA | Sigma, A2103 | 500 |
| Human nuclei | Millipore, MAB1281 | 100 |

Quantitative and Semiquantitative RT-PCR.

RNA was extracted using the RNeasy Plus Mini Kit in combination with QIAshredder (Qiagen). Reverse transcription was performed with 1 µg RNA using iScript cDNA Synthesis Kit (Bio-Rad). Semiquantitative PCR was carried out using Platinum PCR SuperMix (Invitrogen). The primers for the Nurr1, En-1, Hes5, Dach1, Lmx1b, FoxG1, Emx2, Gbx2, HoxB2, HoxA2, Pax3, Nkx2.2, Nkx6.1, and GADPH were as reported (Koch, P., Opitz, T., Steinbeck, J. A., Ladewig, J., and Brustle, O. (2009)). The primers for Otx2 were 5'-CCC TCA CTC GCC ACA TCT AC-3' (SEQ ID NO:1) and 5'-GTT CAG AGT CCT TGG TGG GT-3' (SEQ ID NO:2). Real-time PCR was carried out using iQ SYBR Green Supermix (Bio-Rad). The primers for GAPDH, Oct4, Sox2, Nanog, HoxA5, HoxB4, HoxC5, Isl1, TH, En-1, Pitx3, and Nkx6.1 were as reported (Koch, P., Opitz, T., Steinbeck, J. A., Ladewig, J., and Brustle, O. (2009); Yu, J., Vodyanik, M. A., Smuga-Otto, K., Antosiewicz-Bourget, J., Frane, J. L., Tian, S., Nie, J., Jonsdottir, G. A., Ruotti, V., Stewart, R., et al. (2007)). The primers for Pax6, BMP4, Noggin, Eomes, Brachyury, FoxA2, Sox17, ChAT, Lim3, AADC, SHH, FGF8, and Nurr1 are shown in Table 2. The expression of genes of interest was normalized to that of GAPDH in all samples. After normalization, data were transformed as $\log_{10}$ of the target mRNA signal relative to the untreated control sample.

TABLE 2

| PCR primers used in real-time PCR experiments | | |
|---|---|---|
| Genes | Forward (5'-3') | Reverse (5'-3') |
| Pax6 | CCAGAAAGGATGCCTCATAAA (SEQ ID NO: 3) | TCTGCGCGCCCCTAGTTA (SEQ ID NO: 4) |
| BMP4 | TGAGCCTTTCCAGCAAGTTT (SEQ ID NO: 5) | GCATTCGGTTACCAGGAATC (SEQ ID NO: 6) |
| Noggin | TCGAACACCCAGACCCTATC (SEQ ID NO: 7) | CATGAAGCCTGGGTCGTAGT (SEQ ID NO: 8) |

TABLE 2-continued

PCR primers used in real-time PCR experiments

| Genes | Forward (5'-3') | Reverse (5'-3') |
|---|---|---|
| Eomes | AGGCGCAAATAACAACAACA CC (SEQ ID NO: 9) | ATTCAAGTCCTCCACGCCAT C (SEQ ID NO: 10) |
| Brachyury | TGCTTCCCTGAGACCCAGTT (SEQ ID NO: 11) | GATCACTTCTTTCCTTTGCA TCAAG (SEQ ID NO: 12) |
| FoxA2 | GGGAGCGGTGAAGATGGA (SEQ ID NO: 13) | TCATGTTGCTCACGGAGGAG TA (SEQ ID NO: 14) |
| Sox17 | GGCGCAGCAGAATCCAGA (SEQ ID NO: 15) | CCACGACTTGCCCAGCAT (SEQ ID NO: 16) |
| ChAT | TTTGTCCTCTCCACTAGCCA (SEQ ID NO: 17) | ATACCCATTTGGGACCACAG (SEQ ID NO: 18) |
| Lim3 | GAGGCGACCTGCTGCTA (SEQ ID NO: 19) | GTCCAGGATGTGCTGGTCAC (SEQ ID NO: 20) |
| AADC | AGGAAGCCCTGGAGAGAGAC (SEQ ID NO: 21) | ATTGTCAAAGGAGCAGCATG T (SEQ ID NO: 22) |
| SHH | AGTTTCACTCCTGGCCACTG (SEQ ID NO: 23) | GATGAAGAAAACACCGGAGC (SEQ ID NO: 24) |
| FGF8 | CTCTGCTTCCAAAGGTGTCC (SEQ ID NO: 25) | CAGGTCCTGGCCAACAAG (SEQ ID NO: 26) |
| Nurr1 | AACTGCACTTCGGCAGAGTT (SEQ ID NO: 27) | AAAAGCAATGGGGAGTCCA (SEQ ID NO: 28) |

Electrophysiological Analysis.

Whole-cell recordings with a patch electrode were performed from spontaneously differentiated pNSCs of passage 7 and 25. Data were digitized at 10 kHz with a 2-kHz low-pass Bessel filter. Leakage currents were digitally subtracted using pClamp 10.1 software (Molecular Devices). Synaptic responses were recorded in the voltage clamp mode. The pipette solution for recording synaptic currents contained 120 mM CsCl, 20 mM tetraethylammonium chloride, 10 mM Hepes, 2.25 mM EGTA, 1 mM $CaCl_2$, 2 mM $MgCl_2$, 4 mM MgATP, 0.3 mM GTP, 10 mM phosphocreatine; pH adjusted to 7.2. The bath solution contained 146 mM NaCl, 2.5 mM KCl, 2 mM $CaCl_2$, 10 in M Hepes, 10 mM glucose, 20 mM sucrose; pH 7.4. Inhibitory postsynaptic currents (IPSCs) were pharmacologically isolated by addition of 50 μM 2-amino-5-phosphonovaleric acid (D-APV) and 10 μM 2,3-dihydroxy-6-nitro-7-sulfamoyl-benzo[f]quinoxaline-2,3-dione (NBQX) to the bath solution to block excitatory currents. Excitatory postsynaptic currents (EPSCs) were pharmacologically isolated by addition of 20 μM bicuculline to block inhibitory currents. Data were analyzed using Clampfit 10.1 (Axon Instruments, Union City, Calif.). Action potentials (APs) were recorded in the current-clamp configuration. The pipette solution for recording APs contained 140 mM K-gluconate, 1 mM $MgCl_2$, 10 mM Hepes, 0.25 mM EGTA, 5 mM NaCl, 2 mM MgATP, 0.3 in M Na4GTP 0.3; pH adjusted to 7.2 with KOH. Membrane potential was held at −60 mV. Sodium currents ($I_{Na}$) were elicited by 20-mV voltage steps from a holding potential of −60 mV after prepulse hyperpolarization to −90 mV for 300 ms to remove inactivation. Tetrodotoxin (TTX, 1 μM) was used to block $I_{Na}$.

Microarray Analysis.

The Human Ref-8_v3 expression Beadchip (Illumina) was used for microarray hybridizations to examine the global gene expression of hESCs and pNSCs (passage 6 and passage 27). Biotin-16-UTP labeled cRNA was synthesized from 500 ng of total RNA with the Illumina TotalPrep RNA amplification kit (Ambion AMIL1791, Foster City, Calif.). The hybridization mix containing 750 ng of labeled amplified cRNA was prepared according to the Illumina BeadStation 500× System Manual (Illumina, San Diego, Calif.) using the supplied reagents and GE Healthcare Streptavidin-Cy3 staining solution. Hybridization to the Illumina Human Ref-8_v3 expression Beadchip was for 18 h at 55° C. on a BeadChip Hyb Wheel. The array was scanned using the Illumina BeadArray Reader. All samples were prepared in two biological replicates. Processing and analysis of the microarray data were performed with the Illumina Bead-Studio software and Spotfire software. The data were subtracted for background and normalized using the rank invariant option.

Teratoma Assays.

Teratoma assays were carried out according to the protocol reported on the WiCell Research Institute website: "Teratoma Initiation in hESCs (SOP-CH-213 rev A)". Twenty-six female SCID-beige (4-6 wk, Jackson Laboratory) were transplanted with hESCs (n=2), HUES9-derived pNSCs (n=14), or H1 derived pNSCs (n=10). The animals were observed for teratoma formation for up to six months.

Transplantation and Histology.

pNSCs were transduced by lentiviruses carrying pWPXL (Addgene), a construct expressing EGFP under the control of the EF-1α promoter as reported (Li W, Ding S (2010)). Two to 3 μL of Accutase-dissociated cells ($5\times10^4$ cells per μL) in PBS containing 10% of trypan blue were injected to the lateral ventricle of neonatal (P2-3) mice (n=20) as reported (Lee J P, McKercher S, Muller F J, Snyder E Y (2008)). Thirty days after transplantation, animals were anesthetized and perfused with 4% paraformaldehyde. Brains were isolated and postfixed in 4% paraformaldehyde overnight. After cryoprotection in 30% sucrose solution, brains were frozen and cut on a cryostat (40 μm). Sections were incubated in blocking solution (3% BSA and 0.3% Triton X-100 in PBS). Subsequently, primary antibody (MAP2, 1:1,000, Sigma; GABA, 1:3,000, Sigma; Synaptophysin, 1:500, Millipore; Fos, 1:200, Santa Cruz; NeuN, 1:200, Millipore; GFAP, 1:1,500, DAKO) solution was applied to the sections overnight at room temperature. After three PBS washes, sections were incubated with Alexa Fluor 555-conjugated secondary antibody solution for 30 min at room temperature. Sections were then counterstained with Hoechst dye 33342, and were mounted. Images were captured using an Olympus FV1000 confocal microscope.

Results

Figure 2:
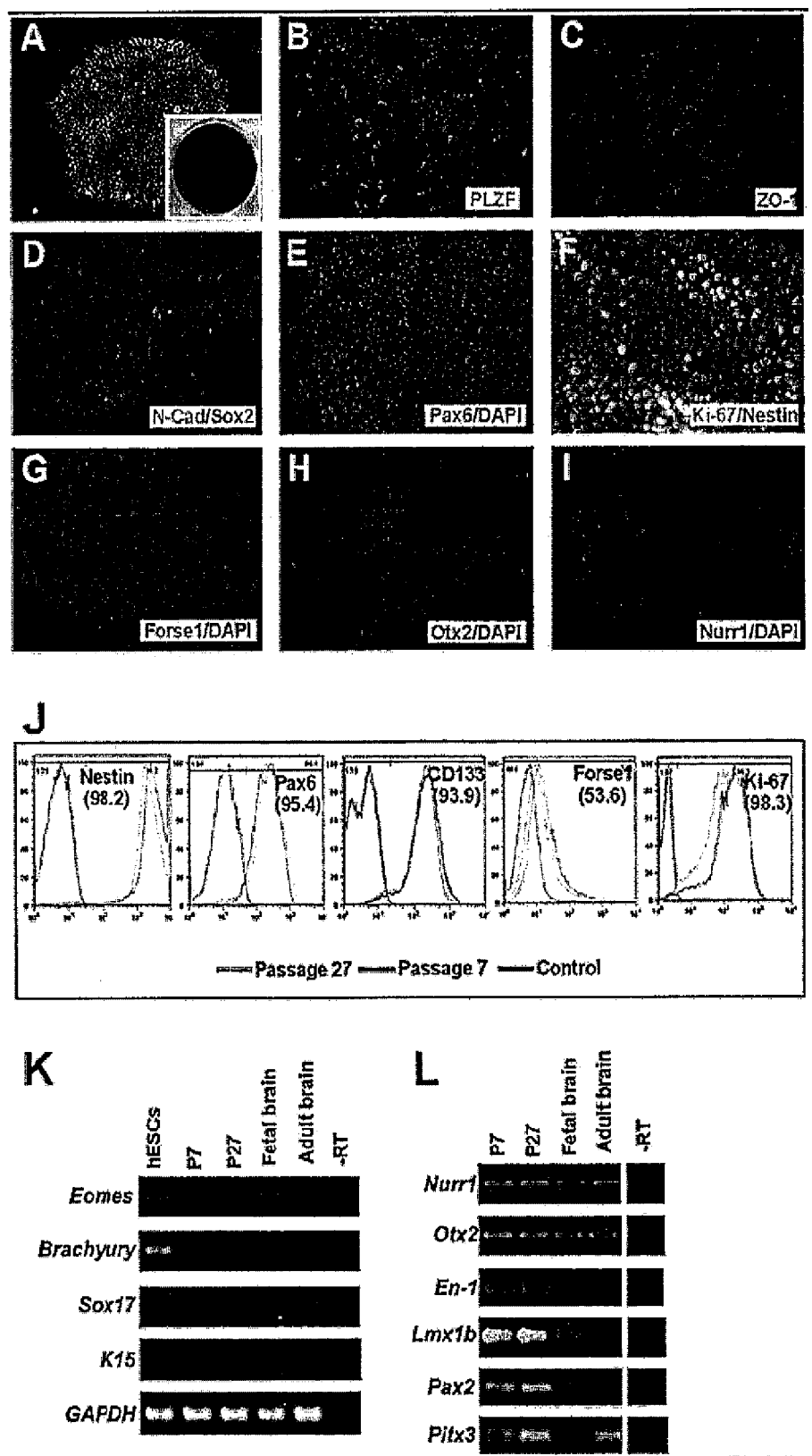
FIG. 2. Primitive neural stem cells (pNSCs) stably self-renew and maintain a homogenous primitive NSC phenotype after long-term cultures. The pNSCs cultured on Matrigel exhibited characteristic epithelial morphology. (A) A single cell-derived pNSC colony on Matrigel. (Inset) pNSCs were positive for ALP. (B-I) Immunocytochemistry showed that pNSCs (passage 6) expressed genes recently identified as rosette-type NSC markers, including PLZF, ZO-1, and N-cad; CNS neural stem cell makers such as Nestin, Pax6, and Sox2; the cell proliferation marker Ki-67; the anterior neural markers Forse1 and Otx2; and the midbrain marker Nurr1. (J) Flow cytometry analysis showed that pNSCs stably expressed NSC and cell proliferation markers after long-term in vitro expansion, including Nestin, Pax6, CD133, Forse1, and Ki-67. (K and L) Non-neural lineage markers and genes associated with midbrain were analyzed by RT-PCR.
Figure 3:
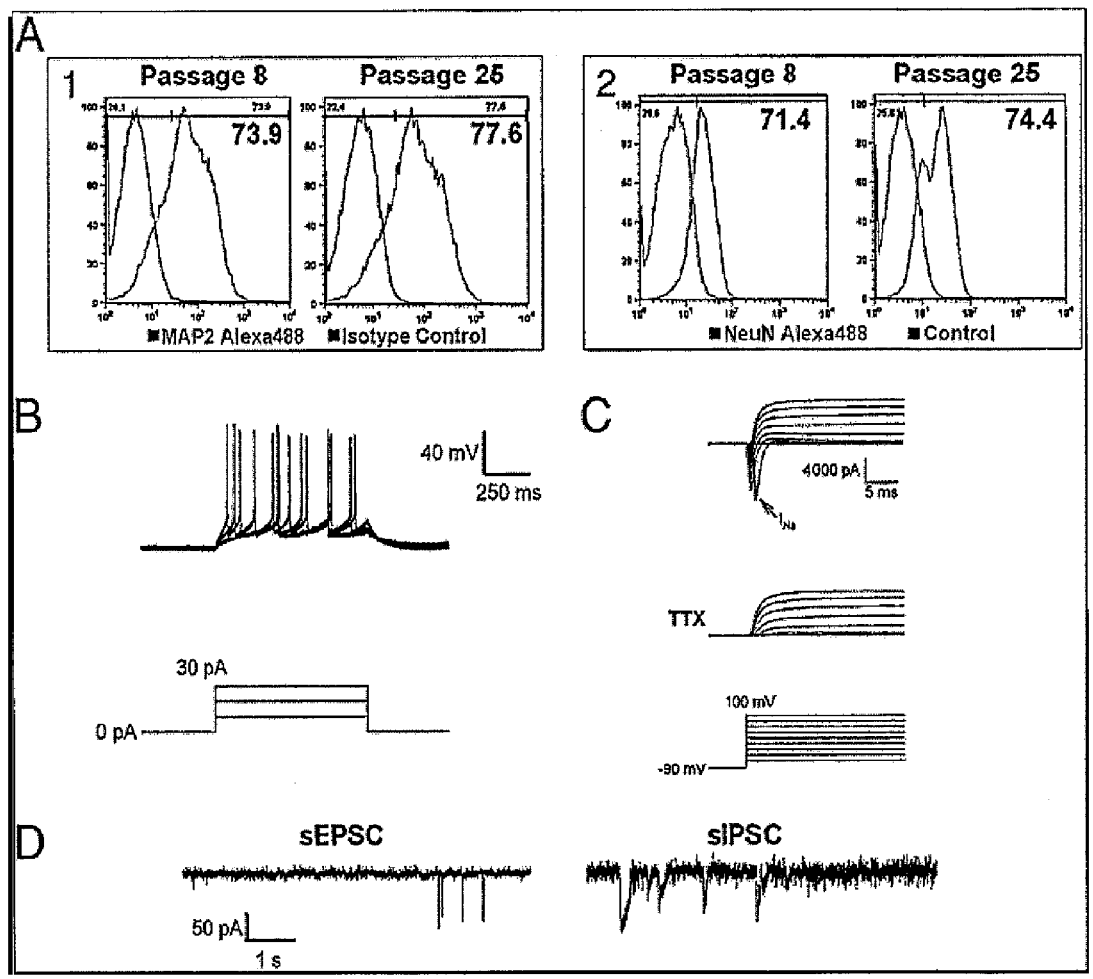
FIG. 3. pNSCs retain high neurogenic potential during long-term culture. (A) Flow cytometry analysis showed pNSCs at passage 8 and passage 25 could give rise to 73.9% and 77.6% MAP2-positive, or 71.4% and 74.4% NeuN-positive neurons, respectively. (B) Representative traces of evoked action potentials (whole-cell recording, current-clamp mode) generated by neurons after 4 wk of differentiation from pNSCs. Traces of Tetrodotoxin (TTX)-sensitive whole-cell currents recorded in voltage-clamp mode. (C) Cells were hyperpolarized to −90 mV for 300 ms before applying depolarizing pulses to elicit Na+ and K+ currents. (D) Traces of spontaneous excitatory postsynaptic currents (sEPSCs) and spontaneous inhibitory postsynaptic currents (sIPSCs), both recorded at a holding potential of −60 mV, indicated synapse formation. B-D represents the data recorded from pNSCs at passage 25 that had spontaneously differentiated to display neuronal properties.
Figure 4:
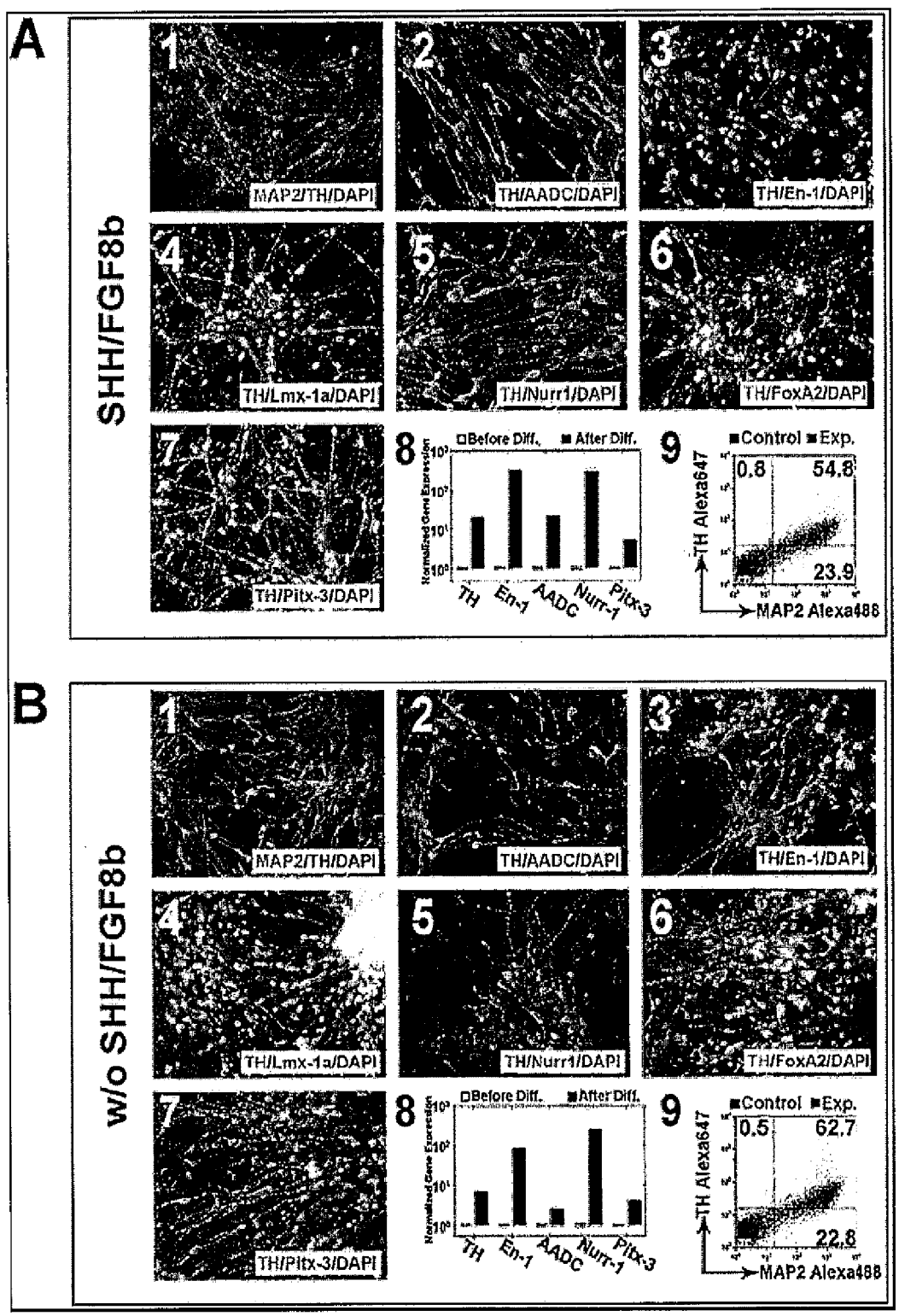
FIG. 4. pNSCs possess mesencephalic regional identity and can differentiate into DA neurons with high efficiency. (A) In the "induced" protocol, pNSCs were treated with Sonic Hedgehog (SHH) and FGF8b for 10 d before they were terminally differentiated in the presence of BDNF, GDNF, IGF1, TGF-β3, and db-cAMP for another ~2-3 wk. (B) In the "default" protocol, pNSCs were directly terminally differentiated in the presence of BDNF, GDNF, IGF1, TGF-β3, and db-cAMP for 3 wk. Under both protocols, pNSCs gave rise to TH positive neurons that also exhibited AADC, En-1, Lmx1a, Nurr1, FoxA2, and Pitx3 immunoreactivity (A 1-7 and B 1-7). Real-time PCR further confirmed the significant up-regulation of TH, AADC, En-1, Nurr1, and Pitx3 (A8 and B8). Flow cytometry quantification demonstrated that the two differentiation protocols produced 54.8% and 62.7% TH and MAP2 double-positive neurons, respectively (A9 and B9).
Figure 5:
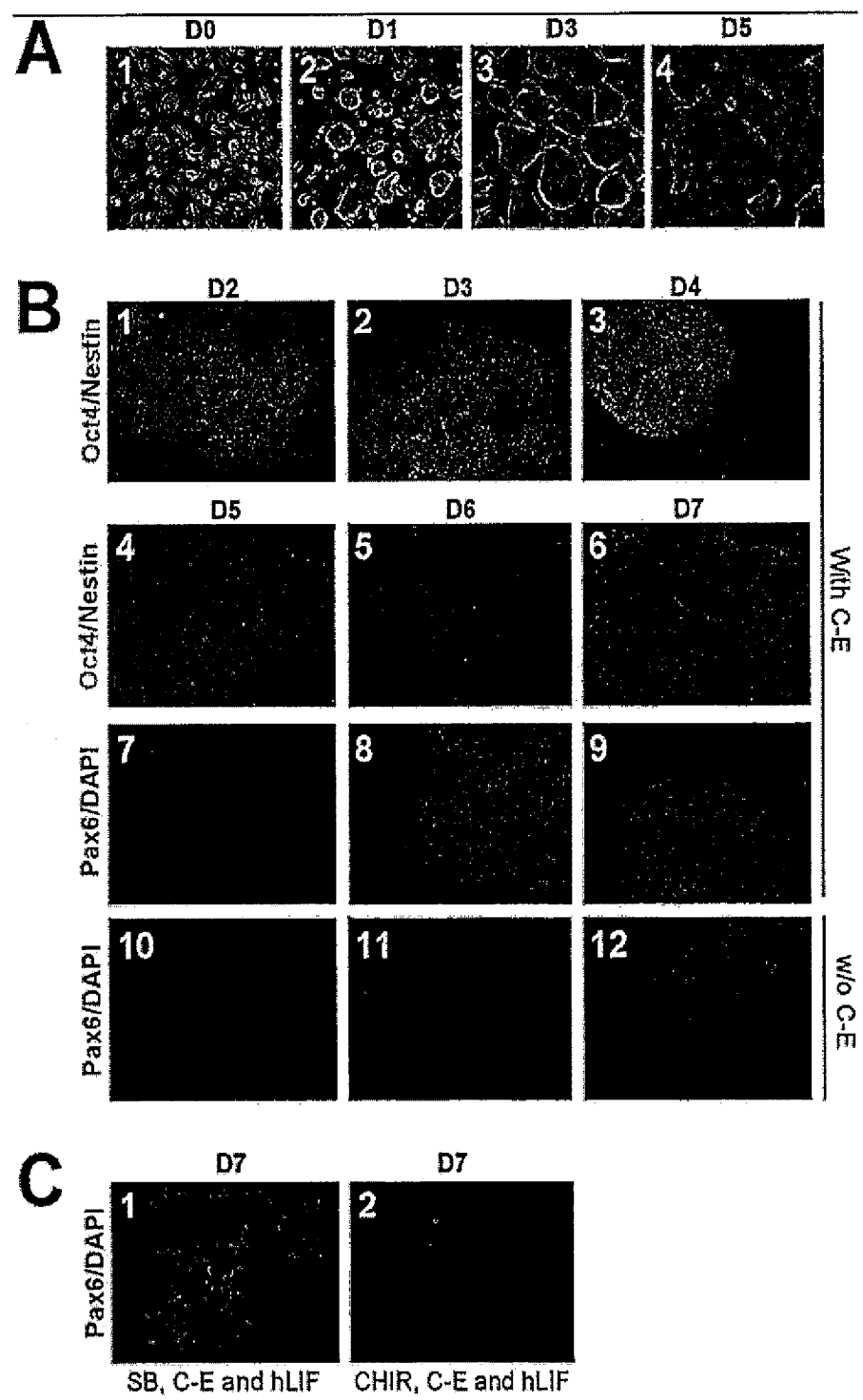
FIG. 5. Characterization of rapid and homogenous neural induction from hESCs. (A) Phase-contrast images of the same visual field during hESC differentiation following CHIR, SB431542, C-E, and hLIF treatment. (B) The expression of Oct4, Nestin, and Pax6 following CHIR, SB, hLIF (with or without C-E) treatment during hESC differentiation was analyzed by immunocytochemistry. (C) The expression of Pax6 was analyzed by immunocytochemistry at day 7 after treatment with SB431542, C-E, and hLIF (C1) or CHIR, C-E and hLIF (C2).

Synergistic Inhibition of GSK3, TGF-β, and Notch Signaling Pathways Converts hESCs into Homogenous pNSCs.

hESCs were cultured on X-ray inactivated CF-1 mouse embryonic fibroblasts (MEFs) in hESC growth media (DMEM/F12 containing 20% KSR and 10 ng/mL bFGF) or on Matrigel under feeder-free and chemically defined conditions as described (Yao, S., Chen, S., Clark, J., Hao, E., Beattie, G. M., Hayek, A., and Ding, S. (2006)). Primitive neuroepithelium was induced by switching from hESC growth media to neural induction media (1:1 Advanced DMEM/F-12:Neurobasal media supplemented with N2, B27, hLIF), supplemented with CHIR and SB431542, with or without C-E, for 7 d (a schematic representation of the differentiation process is shown in FIG. 1A). hESC differentiation was monitored by immunocytochemistry, flow cytometry and real-time PCR. As shown in images of the same visual field, the differentiated cells exhibited homogenous epithelial morphology during the entire differentiation process (FIG. 5A 1-4). Real-time PCR analysis revealed that combined treatment with hLIF, SB431542, and CHIR (with or without C-E) induced a rapid loss of Oct4 and Nanog expression (FIG. 1B). However, the expression of Sox2, a pluripotency marker that is also a persistent marker of NSCs (Ellis, P., Fagan, B. M., Magness, S. T., Hutton, S., Taranova, O., Hayashi, S., McMahon, A., Rao, M., and Pevny, L. (2004)), remained largely unchanged. Pax6, an early marker of neural induction, was significantly up-regulated after 5 d in the presence of C-E (0.1 µM), whereas its up-regulation was first detected at the sixth day in the absence of C-E treatment (FIG. 1B). Consistent with this observation, immunocytochemistry confirmed the faster induction of Pax6 protein on the sixth day in the presence of C-E, as Pax6 protein only became detectable from the seventh day onwards in the absence of C-E (FIG. 5B 7-12). In contrast, only a small fraction of cells were positive for Pax6 on day 7 when hESCs were treated with SB431542, C-E, and hLIF (FIG. 5C1). Similarly, no Pax6 positive cells could be detected at the same time point when hESCs were treated with CHIR, C-E, and hLIF (FIG. 5C2). These data suggest that inhibition of Notch signaling can enhance early neural induction. Interestingly, real-time PCR analysis showed that the induction of the Pax6 gene occurred in parallel with the suppression of BMP4 gene expression as well as induction of Noggin (BMP antagonist) expression (FIG. 1B), suggesting that endogenous mechanisms of BMP signaling inhibition may contribute to neural induction. Real-time PCR analysis also demonstrated that the differentiation is highly specific toward the neural lineage. Along with the induction of Pax6, epiblast-associated non-neural genes such as Brachyury, Eomes, and Sox17, were repressed synchronously with pluripotency markers Oct4 and Nanog (FIG. 1B), suggesting the presence of an intermediate cell type resembling differentiating epiblast cells before hESC neuralization. This highly directed neural induction was further confirmed by immunocytochemistry. Double staining of Oct4 and Nestin showed that Oct4 expression gradually diminished and was almost undetectable after 5 d of treatment with hLIF, SB431542, CHIR, and C-E, whereas Nestin-expressing cells became the predominant population, comprising ~99% of the population on day 7 (FIG. 5B 1-6). To further quantify the efficiency of the neural induction, the expression of Oct4, Sox2 and CD133, was analyzed by flow cytometry. In development, the neural plate and neural tube exhibit CD133 (Prominin-1) immunoreactivity (Marzesco A M, et al. (2005); Corbeil D, et al. (2000)). In vertebrate embryos, Sox2 is one of the earliest markers for the neural plate. During hESC differentiation, the earliest Oct4-negative, but Sox2/CD133-positive cell population would represent the primitive neuroepithelium. FACS analysis showed that more than 96% of undifferentiated hESCs were positive for both Oct4 and Sox2 (FIG. 1C). After treatment, FACS confirmed the rapid loss of Oct4 expression. Especially Oct4-positive cell number dropped substantially on day 5, when Pax6 was first induced, suggesting that day 5 was the turning point of neural induction. In addition, FACS analysis further showed that the addition of C-E induced a much more rapid loss of Oct4 expression and consequent neural conversion. At day 5, only 13% of cells were still positive for Oct4 in the presence of C-E, whereas 33.9% were positive in its absence. Despite the loss of Oct4 expression, cells persistently maintained a high level of Sox2 expression (>96%) at all time points examined during differentiation, and >97% of cells were only positive for Sox2 at day 7 with C-E treatment (FIG. 1C). In addition, FACS analysis showed that 98% of undifferentiated hESCs were positive for CD133 and that small molecule treatment initially induced the loss of CD133. However, along with the induction of Pax6 from day 5 onwards, the CD133-positive cells increased significantly, with >98% cells being CD133-positive on day 9 (FIG. 1D). These homogenously differentiated neural cells could be stably expanded on MEF feeder cells or Matrigel coating in the presence of hLIF, CHIR, and SB431542, and are referred to as pNSCs. In the present study, pNSCs were regularly expanded on Matrigel. Taken together, these data suggested that the combination of hLIF/CHIR/SB431542/C-E directs the specific induction of primitive neuroepithelium within 7 d that can long-term homogenously self-renew under hLIF/CHIR/SB431542 conditions without the need for any cell purification. Chambers et al. ((2009) Nat Biotechnol 27, 275-280) recently demonstrated that dual inhibition of Smad signals by Noggin and SB431542 could convert >80% hESCs to neural fate in 13 d. However, the Noggin/SB431542 condition (which also contains undefined serum products) generated heterogeneous neural populations containing cells of different developmental stages (e.g., nonpolarized neuroepithelia and polarized rosette-like structures). Most importantly, the dual Smad inhibition protocol cannot capture the NSCs and maintain their self-renewal. Our described neural induction process is much faster, more specific, and more efficient, representing a chemically defined single-step strategy for obtaining self-renewing homogenous primitive NSCs from hESCs cultured in a monolayer. The results of our strategy are highly reproducible in multiple different hESC lines, including H1 (FIG. 1), HUES9, and HUES1 (FIG. 6A), under both feeder and feeder-free (Matrigel) culture conditions.

pNSCs can Long-Term Self-Renew and Represent the Pre-Rosette Stage NSCs.

pNSCs can long-term self-renew over serial passages on Matrigel with SBR431542, CHIR, and hLIF. pNSCs generated from HUES9 and H1 hESCs were routinely passaged 1:10 and have been cultured for >30 passages without obviously losing proliferative capacity, which is equivalent to at least 94 population doublings. However, individual omission of hLIF, SB431542, or CHIR from the media compromised pNSCs' long-term self-renewal. Single pNSC is clonogenic on Matrigel in the presence of hLIF/SB431542/CHIR (FIG. 2A). However, no colonies were observed under conditions including C-E, suggesting that Notch signaling is critical to pNSC self-renewal. Consistently, treatment with C-E for 48 h rapidly induced pNSCs to differentiate into Double cortin (DCX)-positive neuronal precursors (FIG. 6B 1 and 2). Despite their highly proliferative and clonogenic capacity, pNSCs are not tumorigenic in SCID beige mice. We transplanted the early-passage (passage 6, about 30 d in serial culture) and late-passage (about passage 27) of HUES9- and H1-derived pNSCs ($2\times10^6$ cells suspended in Matrigel) into 24 SCID beige mice s.c. These mice have been observed for as long as 6 mo with no sign of neoplasm formation, whereas the control animals transplanted with the parental hESCs produced teratomas within 6 wk.

Figure 7:
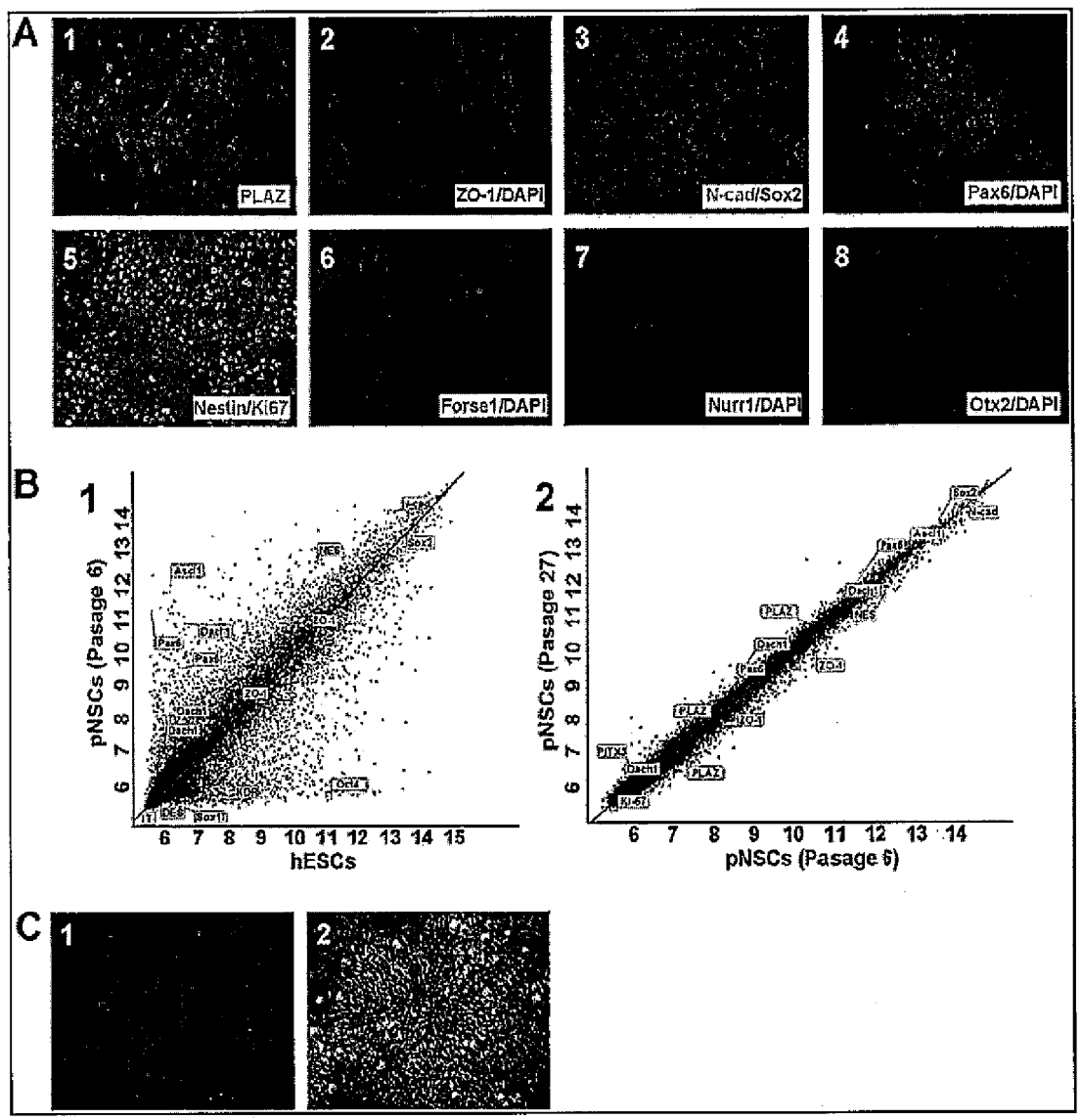
FIG. 7. (A 1-8) Immunocytochemistry showed that pNSCs (passage 27) express genes recently identified as rosette-type NSC markers, including PLZF, ZO-1 and N-cad; CNS neural stem cell makers, such as Nestin, Pax6, and Sox2; cell proliferation marker Ki-67; anterior neural markers Forse1 and Otx2; and midbrain marker Nurr1. The global gene expression of hESCs (HUES9) and pNSCs (passage 6 and passage 27) was analyzed by microarray. B showed the scatter plots between hESCs and passage 6 pNSCs (B 1), and passage 6 pNSCs and passage 27 pNSCs (B2). Microarray analysis confirmed the dramatic up-regulation of neural lineage genes such as Ascl1, Pax6, Dach1, N-cad and Nestin, and down-regulation of pluripotency gene Oct4 in pNSCs in comparison with hESCs (B1). Even after long-term passaging, both early- and late-passage pNSCs demonstrated highly similar transcriptome profile (B2). After long-term passaging, the cells maintained their nonpolarized neuroepithelial morphology (A2 and A3). However, pNSCs gained rosette-like structures after being cultured for 4 d in neural induction media with 20 ng/mL bFGF. (C1) N-cad immunostaining of the rosette-like structure. The phase contrast image of the same visual field is shown in C2. NES, Nestin; T, Brachyury; DES, Desmin; KDR, Kinase insert domain receptor.
Figure 8:
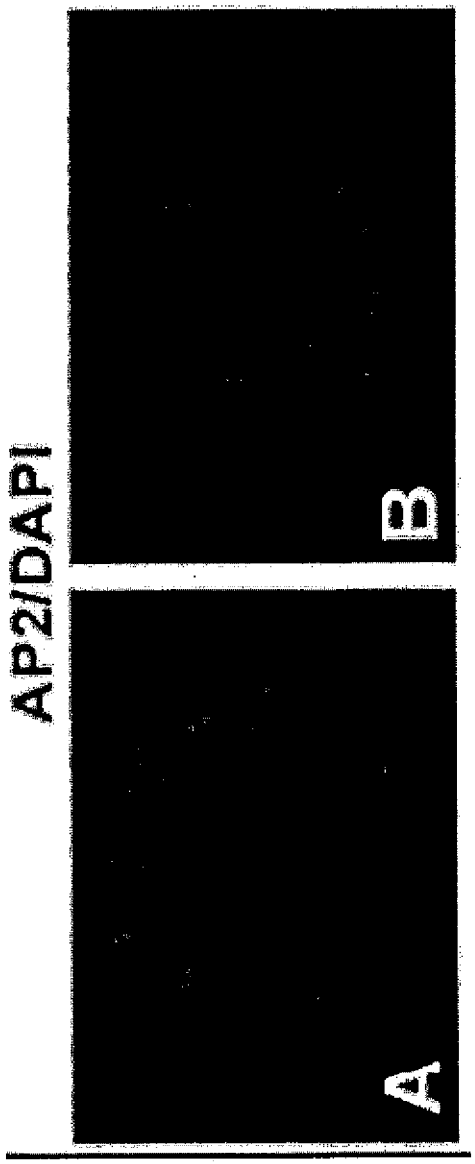
FIG. 8. AP2 expression of single pNSC-derived colonies from early (passage 7, A) or late passages (passage 27, B) were examined by immunocytochemistry.
Figure 9:
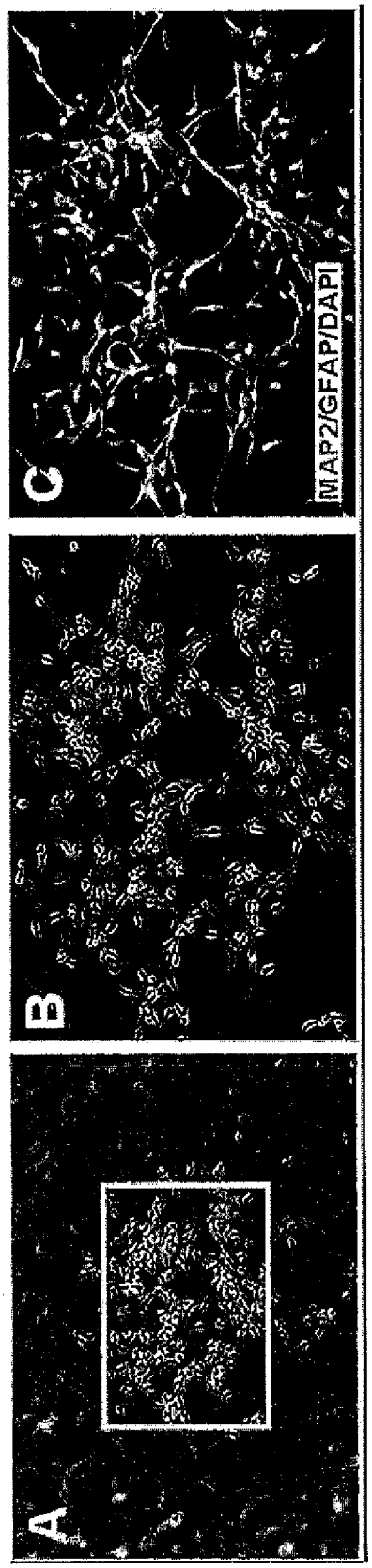
FIG. 9. pNSCs are multipotent NSCs. (A) A single pNSC-derived cell cluster contained both MAP2-positive neurons and GFAP-positive astrocytes after a 2-wk differentiation in neural differentiation medium. (B and C) The boxed area in A.

Remarkably, the long-term expanded pNSCs maintain a stable pNSC phenotype. The pNSCs cultured on Matrigel exhibited typical epithelial morphology and positive ALP staining (FIG. 2A). Immunostaining showed that both the early-passage (passage 6) and late-passage (passage 27) pNSCs stably expressed genes recently identified as rosette-type NSC markers (Elkabetz, Y., Panagiotakos, G., Al Shamy, G., Socci, N. D., Tabar, V., and Studer, L. (2008)), including PLZF (promyelocytic leukemia zinc finger), ZO-1, and N-cad (N-cadherin); CNS (central nervous system) neural stem cell markers, such as Nestin, Pax6, and Sox2; anterior neural markers Forse1 and Otx2; and the midbrain marker Nurr1 (FIG. 2 B-I and FIG. 7A 1-8). Expression analysis by microarray confirmed the dramatic up-regulation of neural lineage genes such as Ascl1, Pax6, Dach1, N-cad, and Nestin, and down-regulation of pluripotency gene Oct4 in pNSCs in comparison to hESCs. However, both hESCs and pNSCs express ZO-1 and Sox2 at similar level. Even after long-term passaging, pNSCs uniformly expressed a panel of primitive neuroepithelial genes, including Sox2, N-cad, PLAZ, Dach1, ZO-1, Pax6, and proneuronal gene Ascl1, and both early and late-passage pNSCs demonstrated highly similar transcriptome profile (FIG. 7B 1 and 2). Notably, N-cad and the tight junction protein ZO-1 were expressed evenly on the surface of both early- and late-passage pNSCs, suggesting that pNSCs are primitive, nonpolarized pre-rosette NSCs (Chambers, S. M., Fasano, C. A., Papapetrou, E. P., Tomishima, M., Sadelain, M., and Studer, L. (2009)). Indeed, pNSCs gained rosette-like structures with apical N-cad expression and interkinetic nuclear migration after being cultured in neural induction media with 20 ng/mL bFGF for 4 d (FIG. 7C 1 and 2). Consistent with their highly proliferative capacity, pNSCs uniformly expressed Ki-67 (FIG. 2F and FIG. 7A5). The stable phenotype of pNSCs after extensive passaging was further confirmed by flow cytometry. Both early-passage and late-passage pNSCs exhibited nearly identical expression patterns for a set of NSC-specific markers, such as Nestin (98.2% positive), Pax6 (95.4% positive), CD133 (93.9% positive), and the cell proliferation marker Ki-67 (98.3% positive; FIG. 2J), whose uniform expression confirmed that pNSCs were a homogenous, expandable NSC population. Indeed, genes associated with non-neural lineages, such as Eomes, Brachyury, Sox17, or K15 were undetectable in pNSCs by RT-PCR (FIG. 2K). FACS analysis with propidium iodide revealed a very similar cell cycle profile for both early- and late-passage of pNSCs. The cell cycle distribution (G1, S, and G2/M) of early-passage pNSCs (P7) is 52.7%, 26.6%, and 16.5%; and the cycle distribution of late-passage pNSCs (P28) is 51.7%, 32.4%, and 12.4%, respectively. Interestingly, FACS analysis showed that the expression of Forse1, an anterior NSC marker, was not homogenous (53.6% of pNSCs were positive for Forse1; FIG. 2J). Whether Forse1-negative pNSCs have a more posterior identity needs to be further characterized. In addition, pNSCs did not express neural crest cell markers such as HNK1, Sox10, or p75. However, we did detect a small percentage (~3%) of pNSCs positive for AP2, a premigratory neural crest gene initially expressed throughout the neural plate border (Gammill L S, Bronner-Fraser M (2003)). To rule out the possibility that pNSC cultures contained a separate (parallel or unrelated) neural crest cell population, we preformed clonal analysis by immunostaining of single pNSC-derived colonies. AP2-positive cells representing 2-5% of cells in each colony were detected in all examined colonies (n=16), and they were mostly seen at the border of the colonies (FIG. 8), suggesting that they were derivatives of pNSCs. However, whether these AP2-positive cells possess neural crest potential remains to be confirmed.

Figure 10:
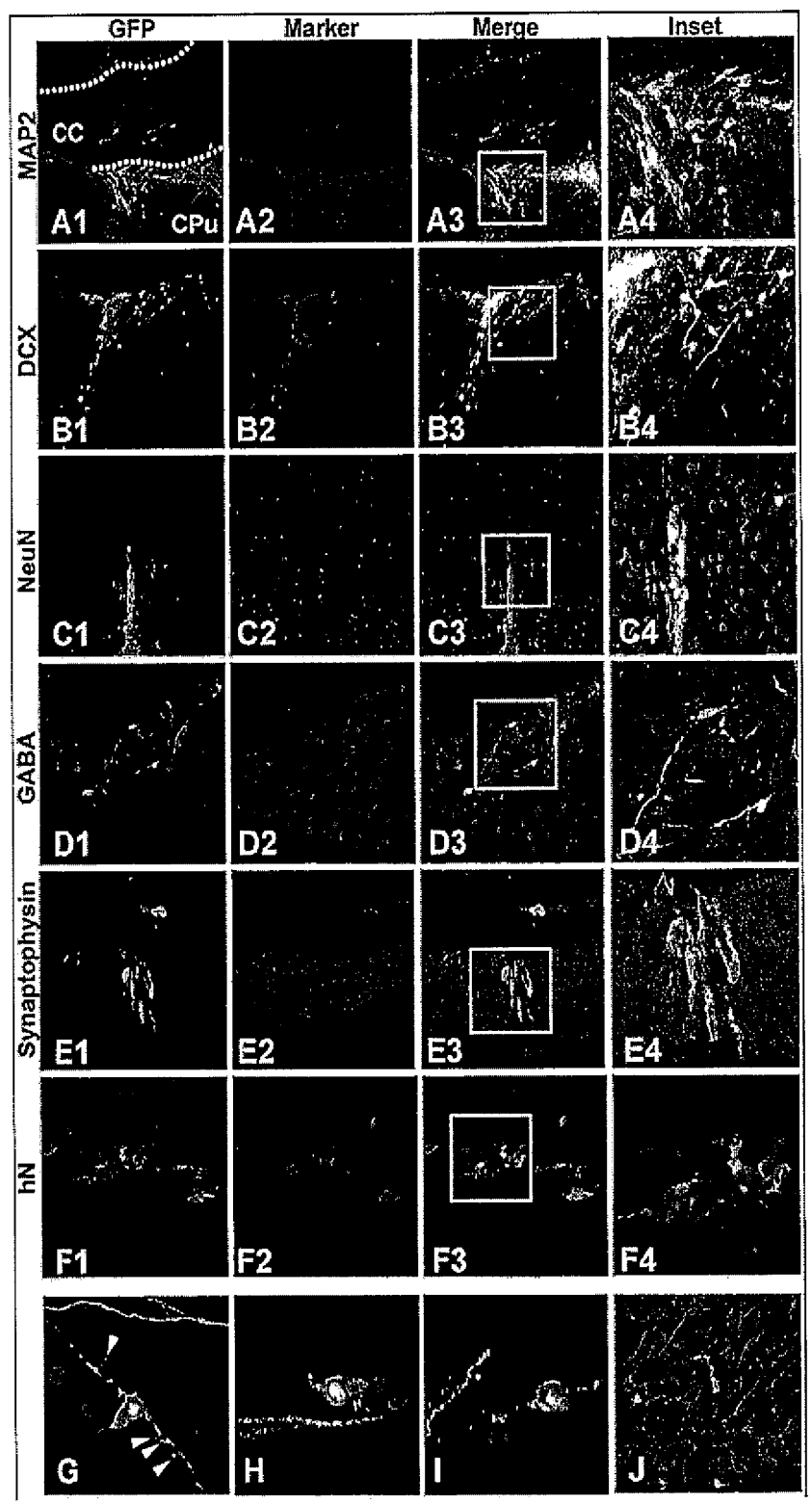
FIG. 10. Transplantation of hESC-derived pNSCs in vivo. Transplanted GFP-expressing pNSCs were distributed in many brain areas, including the corpus callosum, the subcallosal zone, the caudate-putamen (A and B), and the hindbrain (C-J). Engrafted cells expressed neuronal markers such as MAP2 (A1-A4), DCX (B1-B4), NeuN (C1-C4), and GABA (D1-D4). GFP-expressing cells in the hindbrain, closely associated with presynaptic puncta labeled by synaptophysin, were also observed (E1-E4). Engrafted cells also expressed human nucleus antigen (F1-F4), c-fos (G-I), but not the glial marker GFAP (J). A4, B4, C4, D4, E4, and F4 show large magnification images of boxed areas in A3, B3, C3, D3, E3, and F3, respectively. Dotted lines in A3 indicate the borders of the corpus callosum. Arrows in G show dendritic protrusions/spines. (H and I) The ortho-image from a Z-stack of G. CC, corpus callosum; CPu, caudate-putamen; hN, human nucleus antigen.
Figure 11:
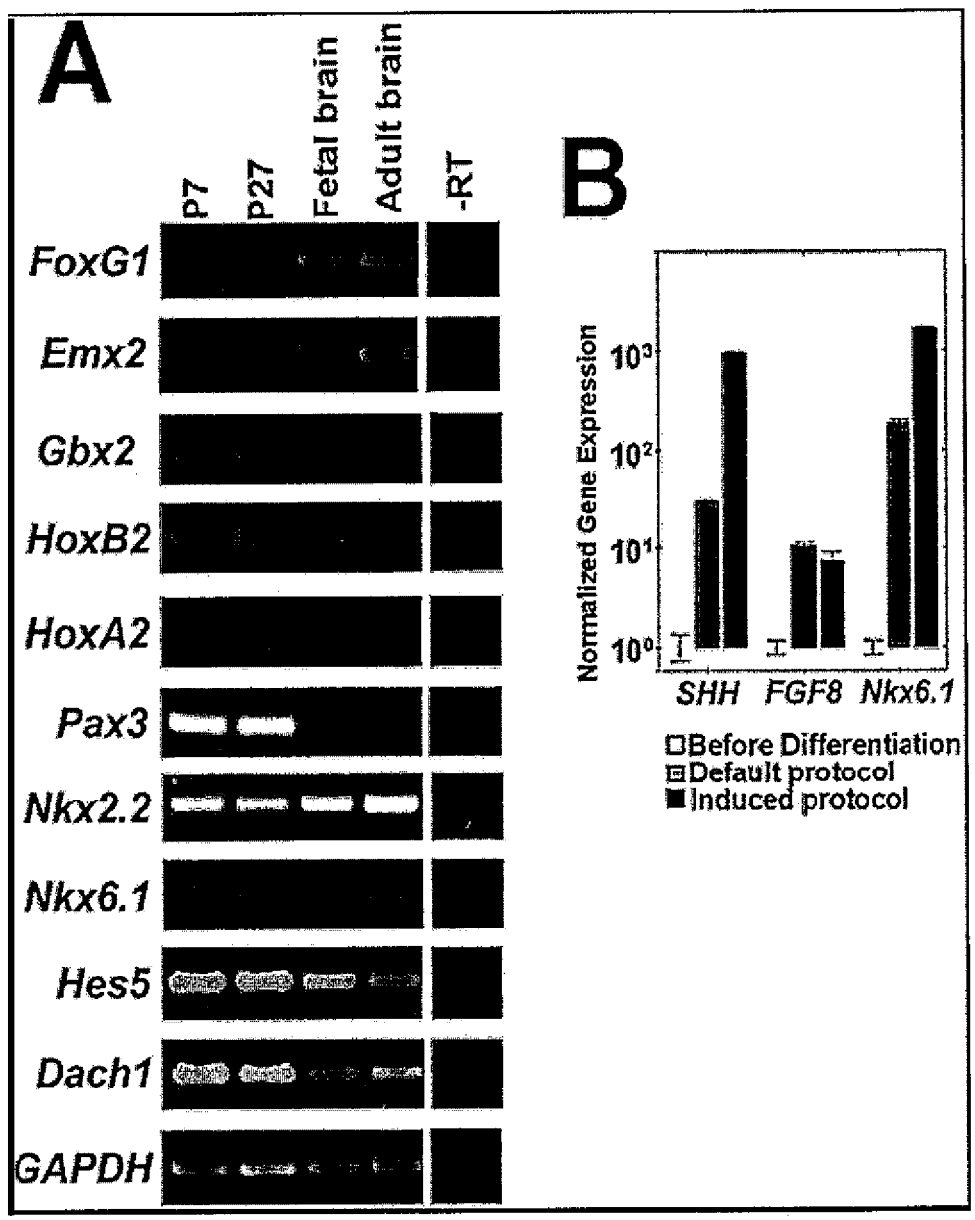
FIG. 11. (A) The expression of a specific set of anterior-posterior and ventral-dorsal neural tube genes was analyzed by RT-PCR. (B) The expression of the endogenous SHH, FGF8, and ventral patterning gene Nkx6.1 in both the "induced" and "default" differentiation protocol was analyzed by real-time PCR.

To examine the multipotency of long-term expanded pNSCs, both early- and late-passage pNSCs were plated at ultra-low density in six-well plates (200 cells per well) and cultured in differentiation media for 2 wk. Among the single pNSC-derived cell clusters (n=29), 100% contained both MAP2-positive neurons and GFAP-positive astrocytes (FIG. 9 A-C), but no cells positive for the oligodendrocyte marker O4 or the neural crest lineage markers peripherin and α-SMA were detected at this time point. Previous studies have shown that bFGF and/or EGF-expanded NSCs lose neurogenic propensity and become more gliogenic after long-term culture (Zhang, S. C. (2006)). However, pNSCs expanded under our described conditions retained high neuronal differentiation propensity. Flow cytometry analysis showed that pNSCs at passage 8 and passage 25 could give rise 73.9% and 77.6% MAP2-positive, or 71.4% and 74.4% NeuN-positive neurons, respectively (FIG. 3A 1 and 2). During CNS development, neurogenesis largely precedes gliogenesis. NSCs from earlier stages generate more neurons and have a lower propensity to produce glia than those from later stages. The remarkably high neurogenic potential and propensity of these long-term expanded pNSCs is consistent with their self-renewal in the primitive state. Importantly, pNSCs could effectively differentiate and generate mature neurons that fired action potentials (5 cells in 7 tested cells; FIG. 3B), and produced fast inactivating inward Na+ currents (n=8 of 8 cells recorded) that were sensitive to the Na+ channel blocker Tetrodotoxin (TTX; FIG. 3C). Furthermore, these differentiated neurons manifested spontaneous excitatory postsynaptic currents (sEPSCs) and/or inhibitory postsynaptic currents (sIPSCs) in 4 of 6 cells recorded (FIG. 3D), indicating that they can form functional synapses. Next, to further examine pNSCs' potential in vivo, they were transplanted into the lateral ventricle of neonatal mice (P2-3). Histological analysis of GFP-expressing pNSC (passage 27) grafts one month after transplantation revealed that engrafted cells were distributed in many brain areas, including the corpus callosum, the subcallosal zone, the caudate-putamen (FIGS. 10 A and B), and the hindbrain (FIG. 10 C-J). Most engrafted cells (>50% in the forebrain, and >80% in the hindbrain) expressed differentiated neuronal markers such as MAP2 (FIG. 10A 1-4). In addition, we also detected DCX-positive engrafted cells in the subcallosal zone (FIG. 10B 1-4), where endogenous adult neural progenitor cells reside (Seri B, et al. (2006)), but not in non-neurogenic environments such as the hindbrain, suggesting that their neuronal differentiation was influenced by the host environment. Although we failed to detect the mature neuronal marker NeuN in the subcallosal zone or caudate-putamen, a subset of GFP-expressing cells in the clusters near the aqueduct exhibited NeuN expression (FIG. 10C 1-4). We also failed to detect spontaneously differentiated tyrosine hydroxylase (TH)-positive dopaminergic (DA) neurons, but some engrafted cells (~10%) appeared to have differentiated into GABA-expressing inhibitory neurons (FIG. 10D 1-4). GFP-expressing cells in the hindbrain, closely associated with presynaptic puncta labeled by synaptophysin, were also observed, indicating the synaptic contacts of the transplanted cells with the host mouse neurons (FIG. 10E 1-4). All GFP positive cells also exhibited human nucleus antigen immunoreactivity (FIG. 10F 1-4), further confirming their human cell identity. In addition, some GFP-expressing hindbrain neurons also exhibited c-fos, a marker for neuronal excitation (FIG. 10 G-I). On the other hand, we did not find any GFAP-positive engrafted cells (FIG. 10J), suggesting that pNSCs preferentially differentiate into the neuronal lineage in vivo.

pNSCs Possess Mesencephalic Regional Identity and can be Re-Specified Toward Caudal Cell Fates.

It is worthwhile to note that pNSCs express the forebrain/midbrain gene Otx2 and the midbrain gene Nurr1 by immunostaining (FIGS. 2 H and I). RT-PCR analysis confirmed the expression of Otx2 and Nurr1, and showed that pNSCs also express other midbrain genes, such as En-1, Lmx1b, Pax2, and Pitx3 (FIG. 2L). In contrast, the forebrain-restricted transcription factors FoxG1 and Emx2 were barely detectable, and anterior hindbrain transcription factors, such as Gbx2, HoxB2, and HoxA2, were expressed at low levels as indicated by RT-PCR (FIG. 11A). pNSCs expressed the dorsal neural tube gene Pax3, the ventral neural tube genes Nkx2.2 and Nkx6.1, the NSC marker Dach1 and the Notch effector Hes5 (FIG. 11A). These observations suggested that in vitro-expanded pNSCs may possess a mesencephalic regional identity. To confirm this, two different differentiation protocols were used to examine the potential of pNSCs to generate midbrain DA neurons: in the "induced" protocol, pNSCs were first treated with 100 ng/mL SHH (Sonic Hedgehog) and 100 ng/mL FGF8b for 10 d and were then further differentiated in the presence of 10 ng/mL BDNF, 10 ng/mL GDNF, 10 ng/mL IGF1, 1 ng/mL TGF-β, and 0.5 mM dibutyryl-cAMP (db-cAMP) for another ~2~3 wk (FIG. 4A). In the "default" protocol, pNSCs were directly terminally differentiated in the presence of BDNF, GDNF, IGF1, TGF-β, and db-cAMP for 3 wk without pre-patterning by morphogens (FIG. 4B). Both the "induced" and "default" differentiation conditions produced >50% TH-positive neurons that also exhibited aromatic L-amino acid decarboxylase (AADC), En-1, Lmx1a, Nurr1, FoxA2, and Pitx3 immunoreactivity (FIG. 4 A 1-7 and B 1-7). Notably, Pitx3 is a homeobox gene uniquely expressed in midbrain DA neurons (Smidt, M. P., van Schaick, H. S. A., Lanctôt, C., Tremblay, J. J., Cox, J. J., van der Kleij, A. A. M., Wolterink, G., Drouin, J., and Burbach, J. P. H. (1997)). Real-time PCR confirmed the significant up-regulation of TH, AADC, En-1, Nurr1, and Pitx3 (FIG. 4 A8 and B8). Flow cytometry quantification demonstrated that the "induced" and "default" differentiation protocols produced 54.8% and 62.7% TH and MAP2 double positive neurons, respectively (FIG. 4 A9 and B9). These data demonstrate that pNSCs possess mesencephalic regional identity and can differentiate into DA neurons with very high efficiency.

Figure 12:
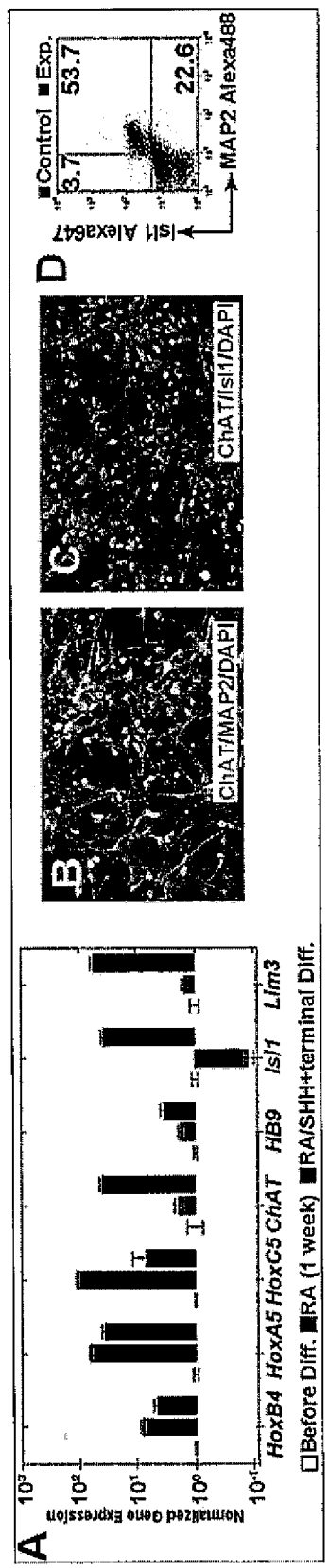
FIG. 12. pNSCs can be re-specified toward caudal cell fates. To re-specify pNSCs toward caudal cell fates, pNSCs were sequentially treated with RA (1 μM), SHH, and RA before being terminally differentiated in the presence of BDNF and GDNF in differentiation media. (A) Real-time PCR assays demonstrated a significant induction of posterior genes, including HoxB4, HoxA5, and HoxC5 after treatment with 1 μM RA for 1 wk; motor neuron markers, including ChAT, HB9, Isl-1, and Lim3 after terminal differentiation. (B and C) Under such conditions, immunocytochemistry showed that pNSCs could differentiate into ChAT positive neurons that are also positive for MAP2 and Isl-1. (D) Flow cytometry analysis showed that 53.7% cells were double-positive for Isl-1 and MAP2.
Figure 13:
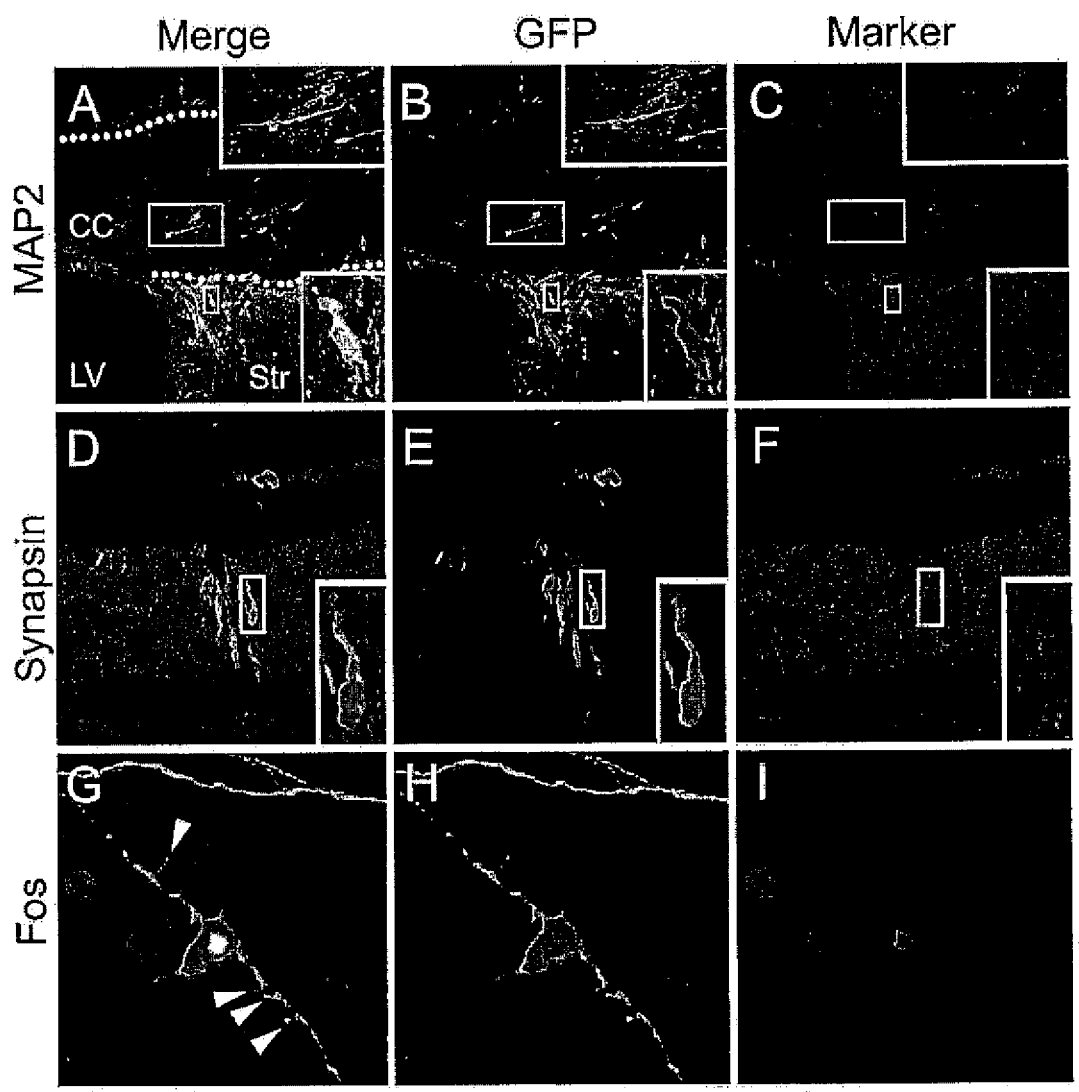
FIG. 13. Transplantation of hESC-derived pNSCs in vivo. Transplanted green fluorescent protein (GFP)-expressing pNSCs widely distributed in many brain areas, including corpus callosum (CC) and caudate-putamen (CPu (also referred to as Str), A-C), hindbrain (D-I) and forebrain and olfactory bulb. One month after transplantation, most transplanted cells expressed differentiated neuronal markers such as MAP2 (A-C). Cells were found to closely associate with presynaptic puncta labeled by synaptophysin (D-F), suggesting the synaptic contacts of transplanted cells with host mouse neurons. In addition, some GFP-expressing neurons also exhibited c-fos, a marker for neuronal excitation (G-I). Insets in A-F show the large magnification images of boxed areas. Dotted lines in A indicate the borders of corpus callosum. Arrows in G show dendritic protrusion/spines. Abbreviations are CC, corpus callosum; LV, lateral ventricle; CPu (also referred to as Str), caudate-putamen.
Figure 14:
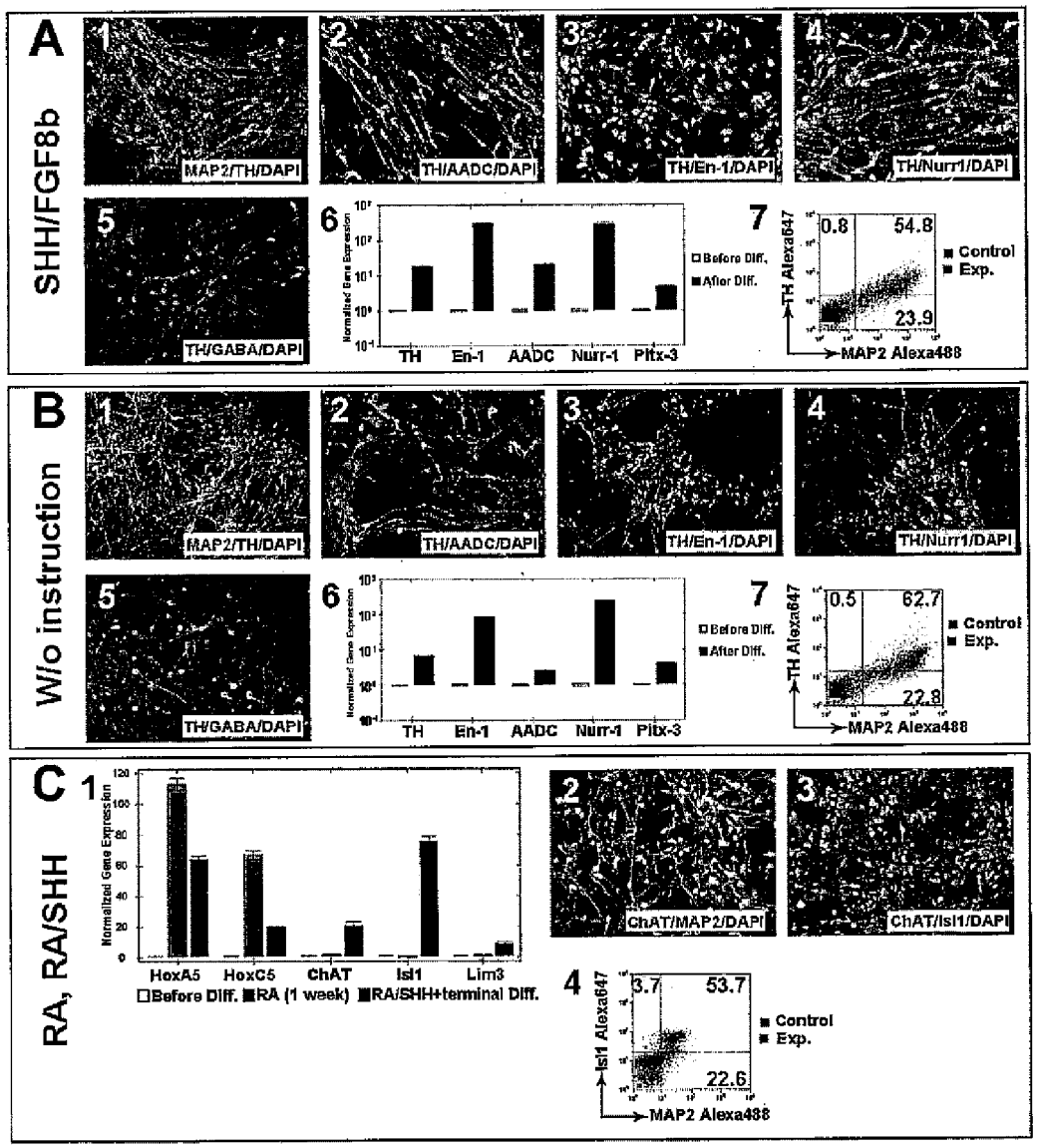
FIG. 14. pNSCs possess mesencephalic regional identity and can be re-specified toward caudal cell fates. In "induced" protocol pNSCs were treated with SHH (Sonic Hedgehog) and FGF8b for 10 days before they were terminally differentiated in the presence of BDGF, GDNF, IGF1, TGF-β3 and db-cAMP for another 2~3 weeks (A). In "default" protocol pNSCs were directly terminally differentiated in the presence of BDGF, GDNF, IGF1, TGF-β3 and db-cAMP for 3 weeks (B). Under both protocols pNSCs gave rise to TH positive neurons that also exhibited AADC, En-1, and Nurr1, but not GABA immunoreactivity. Real-time PCR further confirmed the significant up-regulation of TH, AADC, En-1, Nurr1 and Pitx3. Flow cytometry quantification demonstrated that the two differentiation protocol produced 54.8% and 62.7% TH and MAP2 double positive neurons, respectively (A and B). In addition, pNSCs could differentiate into Isl-1 and ChAT (choline acetyltransferase) double positive motor neurons after pNSCs were sequentially treated with RA, RA/SHH, and terminal differentiation media with BDGF and GDNF (C). Real-time PCR showed the significant induction of posterior genes, including HoxA5 and HoxC5 after pNSCs were treated with RA for one week. After terminal differentiation, in addition to the induction of ChAT, the post-mitotic motor neurons also expressed Isl-1 and Lim-3. Flow cytometry analysis showed that 53.7% differentiated cells were double positive to Isl-1 and MAP2 (C).
Figure 15:
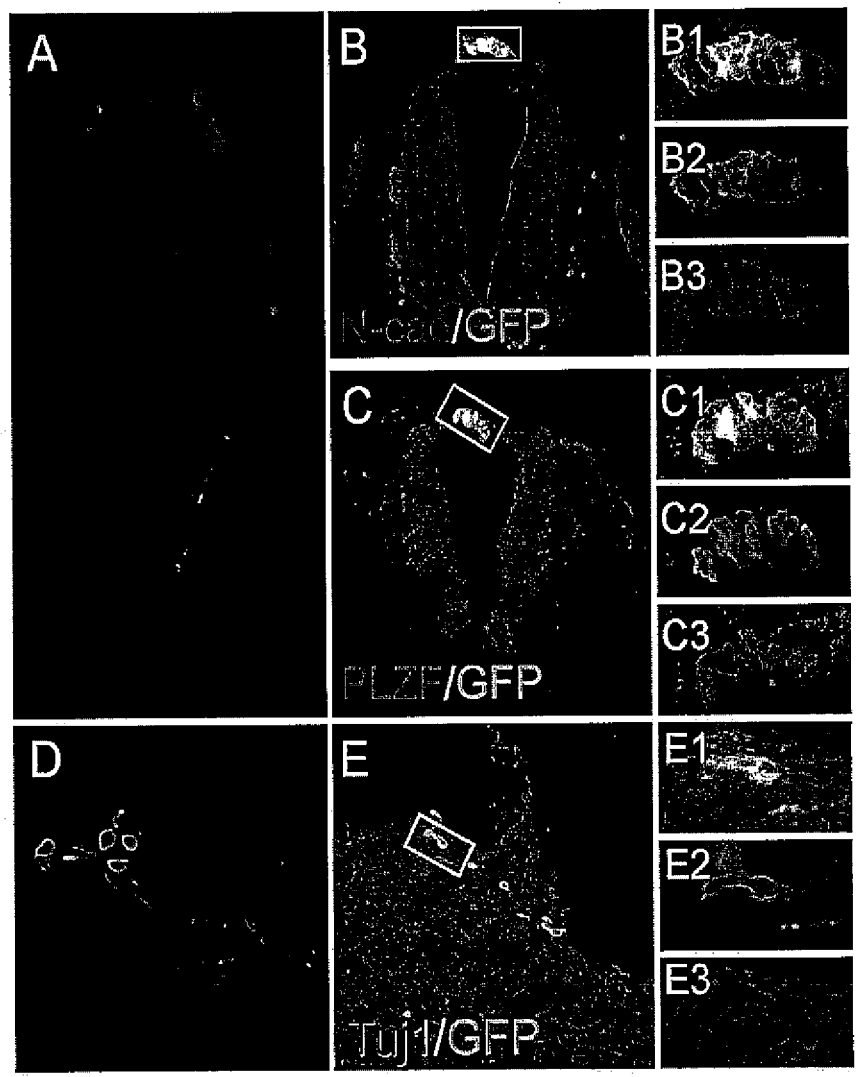
FIG. 15. Transplanted human pNSCs contributed to the host neural tube in chick embryos. Human pNSCs were transplanted to the neural tube of E3 (HH stage 14-16) chick embryos. One day after transplantation, many GFP+ cells were integrated in the neural tube (A). Three days after transplantation, a subset of GFP+ cells were integrated into the host neural tube, and expressed markers for neural tube, such as N-cad (B) or PLZF (C). On the 7th day after transplantation, GFP+ cells could be observed in the spinal cord/hindbrain, exhibited developing neuronal morphology (D), and they expressed neuronal marker, Tuj1 (E). Nuclei were counter-stained with Hoechst33342 (blue). B1-3, C1-3, and E1-3 show the signals from each channel of boxed area.

Because they exhibit features of pre-rosette primitive NSCs, pNSCs were further examined for their responsiveness to instructive regional patterning cues. pNSCs were sequentially treated with caudalizing retinoic acid (RA, 1 μM) for 7 d, 100 ng/mL SHH and 0.1 μMRA for another 7 d, and then 50 ng/mL SHH and 0.1 μM RA for an additional 7 d. The cells were then terminally differentiated in the presence of 10 ng/mL BDNF and 10 ng/mL GDNF in differentiation media for about 7 d. Real-time PCR assays demonstrated significant induction of posterior genes, including HoxB4, HoxA5, and HoxC5 after treatment with 1 μMRA for 1 wk (FIG. 12A), suggesting that pNSCs are responsive to the caudalizing effect of RA. Under such conditions, immunocytochemistry showed that pNSCs could differentiate into choline acetyltransferase (ChAT)-positive neurons that are also positive for MAP2 and Isl-1 (FIGS. 12 B and C). Flow cytometry analysis showed that 53.7% cells were double-positive for Isl-1 and MAP2 (FIG. 12D). Real-time PCR assays confirmed the significant induction of ChAT, HB9, Isl-1, and Lim3 after terminal differentiation (FIG. 12A), suggesting an induction of motor neurons. These data indicated that pNSCs retain responsiveness to instructive cues promoting the induction of hindbrain neuronal subtypes.

Discussion

Interestingly, the neural stem cells of the invention possess features of mesencephalic precursor cells and can differentiate into DA neurons spontaneously with high efficiency in the absence of pre-patterning. Real-time PCR analysis showed the up-regulation of endogenous SHH, FGF8, and the ventral patterning gene Nkx6.1 under both "induced" and "default" differentiation protocols (FIG. 11B), suggesting the cells could be specified into DA neurons by an endogenous mechanism. These observations are reminiscent of the previous in vivo studies that showed DA neurons originated from SHH-expressing domains of the ventral midbrain (Joksimovic M, et al. (2009)). In addition, a mouse study demonstrated the antagonistic interaction between the activation of Wnt/β-catenin and SHH (Tang M, et al. (2010)). The activation of β-catenin in the ventral midbrain promoted the expansion of early DA progenitors, but led to a reduced expression of SHH. The removal of the GSK3 inhibitor (CHIR) during pNSC differentiation may lead to down-regulation of Wnt/β-catenin signaling and facilitate the upregulated SHH expression in turn. Considering the significance of developing renewable sources of DA neurons, it would be useful to examine whether pNSC transplantation could attenuate the Parkinson's symptoms in animal models in the future.

Recent studies suggest that GSK3 plays key roles in many fundamental processes, including mediating signaling downstream of Wnt, FGF, Hedgehog (Hh), and Notch during neural development (Mao Y, et al. (2009); Kim W Y, et al. (2009); Hur E M, Zhou F Q (2010)). In our neural induction protocol, however, replacement of CHIR with Wnt3a induced significant spontaneous differentiation and did not generate a homogenous NSC population, suggesting that GSK3 inhibition may coordinate multiple signals besides canonical Wnt activation in the context of neural induction under this condition. One possible explanation for this specific neural induction is that inhibition of TGF-β/Nodal signaling by SB431542 not only blocks the formation of mesendoderm, but also engages in cross-talk with GSK3-mediated signaling (for example FGF signaling) to enhance neural induction, possibly by modulating a downstream component of endogenous BMP signaling (Chambers, S. M., Fasano, C. A., Papapetrou, E. P., Tomishima, M., Sadelain, M., and Studer, L. (2009), Gerrard L, Rodgers L, Cui W (2005)). In addition, very recent studies showed that GSK3 is a master regulator of in vivo neural progenitor homeostasis (Mao Y, et al. (2009), Kim W Y, et al. (2009)). It is possible that neural induction is also coupled with the capture/maintenance of primitive NSCs through GSK3 inhibition. Specifically, the combination of GSK3 inhibitor, TGF-β receptor inhibitor, and hLIF is uniquely required for long-term self-renewal of pNSCs under chemically defined conditions. Recent in vivo studies demonstrated that TGF-β pathway activation counteracts canonical Wnt and negatively regulates self-renewal of midbrain neuroepithelial stem cells in the developing mouse brain (Falk, S., Wurdak, H., Ittner, L. M., Ille, F., Sumara, G., Schmid, M. T., Draganova, K., Lang, K. S., Paratore, C., Leveen, P., et al. (2008)). Loss of TGF-β signaling results in neuroepithelial expansion in the midbrain, but not the forebrain (Falk, S., Wurdak, H., Ittner, L. M., Ille, F., Sumara, G., Schmid, M. T., Draganova, K., Lang, K. S., Paratore, C., Leveen, P., et al. (2008)). The use of GSK3 inhibitor (which can activate canonical Wnt) and TGF-β receptor inhibitor may partly recapitulate such in vivo self-renewal signals of midbrain NSCs. This strategy could also be generalized and applied to the capture of self-renewing stem cells from other germ layers, such as endoderm or mesoderm. Finally, this protocol also provides a valuable tool with which to study the early molecular events initiating human neural induction.

REFERENCES

Baker, J. C., Beddington, R. S., and Harland, R. M. (1999). Wnt signaling in *Xenopus* embryos inhibits bmp4 expression and activates neural development. Genes Dev 13, 3149-3159.

Bakre, M. M., Hoi, A., Mong, J. C., Koh, Y. Y., Wong, K. Y., and Stanton, L. W. (2007). Generation of multipotential mesendodermal progenitors from mouse embryonic stem cells via sustained Wnt pathway activation. J Biol Chem 282, 31703-31712.

Camus, A., Perea-Gomez, A., Moreau, A., and Collignon, J. (2006). Absence of Nodal signaling promotes precocious neural differentiation in the mouse embryo. Dev Biol 295, 743-755.

Chambers, S. M., Fasano, C. A., Papapetrou, E. P., Tomishima, M., Sadelain, M., and Studer, L. (2009). Highly efficient neural conversion of human ES and iPS cells by dual inhibition of SMAD signaling. Nat Biotechnol 27, 275-280.

Elkabetz, Y., Panagiotakos, G., Al Shamy, G., Socci, N. D., Tabar, V., and Studer, L. (2008). Human ES cell-derived neural rosettes reveal a functionally distinct early neural stem cell stage. Genes Dev 22, 152-165.

Elkabetz, Y., and Studer, L. (2008). Human ESC-derived neural rosettes and neural stem cell progression. Cold Spring Harb Symp Quant Biol 73, 377-387.

Ellis, P., Fagan, B. M., Magness, S. T., Hutton, S., Taranova, O., Hayashi, S., McMahon, A., Rao, M., and Pevny, L. (2004). SOX2, a persistent marker for multipotential neural stem cells derived from embryonic stem cells, the embryo or the adult. Dev Neurosci 26, 148-165.

Falk, S., Wurdak, H., Ittner, L. M., Ille, F., Sumara, G., Schmid, M. T., Draganova, K., Lang, K. S., Paratore, C., Leveen, P., et al. (2008). Brain area-specific effect of TGF-beta signaling on Wnt-dependent neural stem cell expansion. Cell Stem Cell 2, 472-483.

Gomez-Skarmeta, J., de La Calle-Mustienes, E., and Modolell, J. (2001). The Wnt-activated Xiro1 gene encodes a repressor that is essential for neural development and downregulates Bmp4. Development 128, 551-560.

Harland, R. (2000). Neural induction. Curr Opin Genet Dev 10, 357-362.

Hitoshi, S., Alexson, T., Tropepe, V., Donoviel, D., Elia, A. J., Nye, J. S., Cordon, R. A., Mak, T. W., Bernstein, A., and van der Kooy, D. (2002). Notch pathway molecules are essential for the maintenance, but not the generation, of mammalian neural stem cells. Genes Dev 16, 846-858.

Hitoshi, S., Seaberg, R. M., Koscik, C., Alexson, T., Kusunoki, S., Kanazawa, I., Tsuji, S., and van der Kooy, D. (2004). Primitive neural stem cells from the mammalian epiblast differentiate to definitive neural stem cells under the control of Notch signaling. Genes Dev 18, 1806-1811.

Kalani, M. Y. S., Cheshier, S. H., Cord, B. J., Bababeygy, S. R., Vogel, H., Weissman, I. L., Palmer, T. D., and Nusse, R. (2008). Wnt-mediated self-renewal of neural stem/progenitor cells. Proceedings of the National Academy of Sciences 105, 16970-16975.

Koch, P., Opitz, T., Steinbeck, Ladewig, J., and Brustle, O. (2009). A rosette-type, self-renewing human ES cell-derived neural stem cell with potential for in vitro instruction and synaptic integration. Proc Natl Acad Sci USA 106, 3225-3230.

Li, W., Wei, W., Zhu, S., Zhu, J., Shi, Y., Lin, T., Hao, E., Hayek, A., Deng, H., and Ding, S. (2009). Generation of rat and human induced pluripotent stem cells by combining genetic reprogramming and chemical inhibitors. Cell Stem Cell 4, 16-19.

Masayoshi, T., Yoshio, H., Aki, H., Tetsuya, K., Masao, S., Kohei, M., Manabu, N., and Takeshi, I. (2005). The ALK-5 inhibitor A-83-01 inhibits Smad signaling and epithelial-to-mesenchymal transition by transforming growth factor-β. Cancer Science 96, 791-800.

Michaelidis, T., and Lie, D. (2008). Wnt signaling and neural stem cells: caught in the Wnt web. Cell and Tissue Research 331, 193-210.

Pankratz, M. T., Li, X. J., Lavaute, T. M., Lyons, E. A., Chen, X., and Zhang, S. C. (2007). Directed neural differentiation of human embryonic stem cells via an obligated primitive anterior stage. Stem Cells 25, 1511-1520.

Qian, X., Shen, Q., Goderie, S. K., He, W., Capela, A., Davis, A. A., and Temple, S. (2000). Timing of CNS cell generation: a programmed sequence of neuron and glial cell production from isolated murine cortical stem cells. Neuron 28, 69-80.

Ring, D. B., Johnson, K. W., Henriksen, E. J., Nuss, J. M., Goff, D., Kinnick, T. R., Ma, S. T., Reeder, L. W., Samuels, I., Slabiak, T., et al. (2003). Selective Glycogen Synthase Kinase 3 Inhibitors Potentiate Insulin Activation of Glucose Transport and Utilization In Vitro and In Vivo. Diabetes 52, 588-595.

Sato, N., Meijer, L., Skaltsounis, L., Greengard, P., and Brivanlou, A. H. (2004). Maintenance of pluripotency in human and mouse embryonic stem cells through activation of Wnt signaling by a pharmacological GSK-3-specific inhibitor. Nat Med 10, 55-63.

Seiffert, D., Bradley, J. D., Rominger, C. M., Rominger, D. H., Yang, F., Meredith, J. E., Wang, Q., Roach, A. H., Thompson, L. A., Spitz, S. M., et al. (2000). Presenilin-1 and -2 Are Molecular Targets for γ-Secretase Inhibitors. Journal of Biological Chemistry 275, 34086-34091.

Smidt, M. P., van Schaick, H. S. A., Lanctôt, C., Tremblay, J. J., Cox, J. J., van der Kleij, A. A. M., Wolterink, G., Drouin, J., and Burbach, J. P. H. (1997). A homeodomain gene Ptx3 has highly restricted brain expression in mesencephalic dopaminergic neurons. Proceedings of the National Academy of Sciences of the United States of America 94, 13305-13310.

Smukler, S. R., Runciman, S. B., Xu, S., and van der Kooy, D. (2006). Embryonic stem cells assume a primitive neural stem cell fate in the absence of extrinsic influences. J Cell Biol 172, 79-90.

Sonntag, K. C., and Sanchez-Pernaute, R. (2006). Tailoring human embryonic stem cells for neurodegenerative disease therapy. Curr Opin Investig Drugs 7, 614-618.

Tao, W., and Lai, E. (1992). Telencephalon-restricted expression of BF-1, a new member of the HNF-3/fork head gene family, in the developing rat brain. Neuron 8, 957-966.

Tropepe, V., Hitoshi, S., Sirard, C., Mak, T. W., Rossant, J., and van der Kooy, D. (2001). Direct neural fate specification from embryonic stem cells: a primitive mammalian neural stem cell stage acquired through a default mechanism. Neuron 30, 65-78.

Wobus, A. M., and Boheler, K. R. (2005). Embryonic Stem Cells: Prospects for Developmental Biology and Cell Therapy. Physiol Rev 85, 635-678.

Yao, S., Chen, S., Clark, J., Hao, E., Beattie, G. M., Hayek, A., and Ding, S. (2006). Long-term self-renewal and directed differentiation of human embryonic stem cells in chemically defined conditions. 103, 6907-6912.

Yu, J., Vodyanik, M. A., Smuga-Otto, K., Antosiewicz-Bourget, J., Frane, J. L., Tian, S., Nie, J., Jonsdottir, G. A., Ruotti, V., Stewart, R., et al. (2007). Induced pluripotent stem cell lines derived from human somatic cells. Science 318, 1917-1920.

Zhang, S. C. (2006). Neural subtype specification from embryonic stem cells. Brain Pathol 16, 132-142.

Conti L, Cattaneo E (2010) Neural stem cell systems: physiological players or in vitro entities? Nat Rev Neurosci 11:176-187.

Marzesco A M, et al. (2005) Release of extracellular membrane particles carrying the stem cell marker prominin-1 (CD133) from neural progenitors and other epithelial cells. J Cell Sci 118:2849-2858.

Corbeil D, et al. (2000) The human AC133 hematopoietic stem cell antigen is also expressed in epithelial cells and targeted to plasma membrane protrusions. J Biol Chem 275:5512-5520.

Gammill L S, Bronner-Fraser M (2003) Neural crest specification: migrating into genomics. Nat Rev Neurosci 4:795-805.

Seri B, et al. (2006) Composition and organization of the SCZ: a large germinal layer containing neural stem cells in the adult mammalian brain. Cereb Cortex 16(Suppl 1):i103-i111.

Joksimovic M, et al. (2009) Spatiotemporally separable Shh domains in the midbrain define distinct dopaminergic progenitor pools. Proc Natl Acad Sci USA 106:19185-19190.

Tang M, et al. (2010) Interactions of Wnt/beta-catenin signaling and sonic hedgehog regulate the neurogenesis of ventral midbrain dopamine neurons. J Neurosci 30:9280-9291.

Mao Y, et al. (2009) Disrupted in schizophrenia 1 regulates neuronal progenitor proliferation via modulation of GSK3beta/beta-catenin signaling. Cell 136:1017-1031.

Kim W Y, et al. (2009) GSK-3 is a master regulator of neural progenitor homeostasis. Nat Neurosci 12:1390-1397.

Hur E M, Zhou F Q (2010) GSK3 signalling in neural development. Nat Rev Neurosci 11:539-551.

Gerrard L, Rodgers L, Cui W (2005) Differentiation of human embryonic stem cells to neural lineages in adherent culture by blocking bone morphogenetic protein signaling. Stem Cells 23:1234-1241.

Li W, Ding S (2010) Generation of novel rat and human pluripotent stem cells by reprogramming and chemical approaches. Methods Mol Biol 636:293-300.

Lee J P, McKercher S, Muller F J, Snyder E Y (2008) Neural stem cell transplantation in mouse brain. Curr Protoc Neurosci (John Wiley and Sons, Hoboken, N.J.) Chapter 3: Unit 3.10.

What is claimed is:

1. A method for obtaining neural stem cells substantially free of non-neural stem cells from a mammalian embryonic or inducible pluripotent stem cell population comprising:
   a. culturing mammalian embryonic or inducible pluripotent stem cells in a cell culture medium having a leukemia inhibitory factor (LIF), an inhibitor of glycogen synthase kinase 3 (GSK3), and an inhibitor of transforming growth factor β (TGF-β) under suitable conditions so as to differentiate the cells so cultured into neural stem cells; and
   b. obtaining neural stem cells from step (a) above which are substantially free of non-neural stem cells.

2. The method of claim 1 further comprising an inhibitor of a Notch Signaling Pathway.

3. The method of claim 1, wherein the cell culture medium is free of feeder cells.

4. The method of claim 1, wherein the inhibitors are selected from a group consisting of small molecules, proteins, peptides, antibodies and nucleic acids.

5. The method of claim 1, wherein the GSK3 inhibitor is selected from a group consisting of CHIR99021 (6-(2-(4-(2,4-dichlorophenyl)-5-(4-methyl-1H-imidazol-2-yl)pyrimidin-2-ylamino)ethylamino)nicotinonitrile), 1-azakenpaullone (9-Bromo-7,12-dihydro-pyrido[3',2':2,3]azepino[4,5-b]indol-6(5H)-one), BIO ((2'Z,3'E)-6-Bromoindirubin-3'-oxime), AR-A014418 (N-(4-Methoxybenzyl)-N'-(5-nitro-1,3-thiazol-2-yl)urea), Indirubin-3'-monoxime, 5-Iodo-indirubin-3'-monoxime, kenpaullone (9-Bromo-7,12-dihydroindolo-[3,2-d][1]benzazepin-6(5H)-one), SB-415286 (3-[(3-Chloro-4-hydroxyphenyl)amino]-4-(2-nitro-phenyl)-1H-pyrrole-2,5-dione), SB-216763 (3-(2,4-Dichlorophenyl)-4-(1-methyl-1H-indol-3-yl)-1H-pyrrole-2,5-dione), Maybridge SEW00923 SC (2-anilino-5-phenyl-1,3,4-oxadiazole), (Z)-5-(2,3-Methylenedioxyphenyl)imidazolidine-2,4-dione, and lithium salt.

6. The method of claim 1, wherein the TGFβ inhibitor is selected from a group consisting of SB431542 (4-[4-(1,3-benzodioxol-5-yl)-5-(2-pyridinyl)-1H-imidazol-2-yl]benzamide), A 83-01 (3-(6-Methyl-2-pyridinyl)-N-phenyl-4-(4-quinolinyl)-1H-pyrazole-1-carbothioamide), SJN 2511 (2-(3-(6-Methylpyridine-2-yl)-1H-pyrazol-4-yl)-1,5-naphthyridine), D 4476 (4-[4-(2,3-Dihydro-1,4-benzodioxin-6-yl)-5-(2-pyridinyl)-1H-imidazol-2-yl]benzamide), LY 364947 (4-[3-(2-Pyridinyl)-1H-pyrazol-4-yl]-quinoline), SB 525334 (6-[2-(1,1-Dimethylethyl)-5-(6-methyl-2-pyridinyl)-1H-imidazol-4-yl]quinoxaline), SD 208 (2-(5-Chloro-2-fluorophenyl)-4-[(4-pyridyl)amino]pteridine), LDN-193189 (4-(6-(4-(piperazin-1-yl)phenyl)pyrazolo[1,5-a]pyrimidin-3-yl)quinoline).

7. The method of claim 2, wherein the inhibitor of a Notch Signaling Pathway is selected from a group consisting of Compound E ((S,S)-2-[2-(3,5-Difluorophenyl)-acetylamino]-N-(1-methyl-2-oxo-5-phenyl-2,3-dihydro-1H- benzo[e][1,4]diazepin-3-yl)-propionamide), DAPT (N-[(3,5-Difluorophenyl)acetyl]-L-alanyl-2-phenyl]glycine-1,1-dimethylethyl ester), LY411575 ((aS)—N-[(1S)-2-[[(7S)-6,7-Dihydro-5-methyl-6-oxo-5H-dibenz[b,d]azepin-7-yl]amino]-1-methyl-2-oxoethyl]-3,5-difluoro-alpha-hydroxybenzeneacetamide), MK0752 (3-((1S,3S)-3-((4-chlorophenyl)sulfonyl)-4-(2,5-difluorophenyl)cyclohexyl) propanoic acid), RO4929097 (2,2-dimethyl-N-(6-oxo-6,7-dihydro-5H-dibenzo[b,d]azepin-7-yl)-N'-(2,2,3,3,3-pentafluoropropyl)malonamide), PF-03084014 ((S)-2-(((S)-6,8-difluoro-1,2,3,4-tetrahydronaphthalen-2-yl)amino)-N-(1-(2-methyl-1-(neopentylamino)propan-2-yl)-1H-imidazol-4-yl)pentanamide), LY450139 ((2S)-2-hydroxy-3-methyl-N-[(1S)-1-{[(1S)-3-methyl-2-oxo-2,3,4,5-tetrahydro-1H-3-benzazepin-1-yl]carbamoyl}ethyl] butanamide), and γ-Secretase Inhibitor XIX ((2S,3R)-3-(3,4-Difluorophenyl)-2-(4-fluorophenyl)-4-hydroxy-N-((3S)-2-oxo-5-phenyl-2,3-dihydro-1H-benzo[e][1,4]diazepin-3-yl)-butyramide).

8. The method of claim 1, wherein the neural stem cells self-renew and stably maintain their neural precursor or progenitor characteristics over at least 8 passages without differentiating into mature neurons.

9. The method of claim 1, wherein the neural stem cells self-renew and stably maintain their neural precursor or progenitor characteristics over at least 30 passages without differentiating into mature neurons.

10. The method of claim 1, wherein the isolated neural stem cells are obtained within about 7 days of cell culture of the embryonic or inducible pluripotent stem cells.

11. The method of claim 1, wherein the cell culture medium further comprises a ROCK inhibitor to enhance cell survival.

12. The method of claim 11, wherein the ROCK inhibitor is selected from a group consisting of Y-27632 (4-[(1R)-1-aminoethyl]-N-4-pyridinyl-trans-cyclohexanecarboxamide, dihydrochloride), or $C_{22}H_{24}N_4O_4$ (N-(2-(2-(dimethylamino)ethoxy)-4-(1H-pyrazol-4-yl)phenyl)-2,3-dihydrobenzo[b][1,4]dioxine-2-carboxamide).

13. The method of claim 1, wherein the isolated neural stem cells from step (a) have a CD marker profile comprising:
 a. Sox2,
 b. CD133, and
 c. low or undetectable levels of Oct4.

* * * * *

SEQUENCE LISTING

```
<160> NUMBER OF SEQ ID NOS: 28

<210> SEQ ID NO 1
<211> LENGTH: 20
<212> TYPE: DNA
<213> ORGANISM: Artificial Sequence
<220> FEATURE:
<223> OTHER INFORMATION: Otx2 forward primer

<400> SEQUENCE: 1
ccctcactcg ccacatctac                                              20

<210> SEQ ID NO 2
<211> LENGTH: 20
<212> TYPE: DNA
<213> ORGANISM: Artificial Sequence
<220> FEATURE:
<223> OTHER INFORMATION: Otx2 reverse primer

<400> SEQUENCE: 2
gttcagagtc cttggtgggt                                              20

<210> SEQ ID NO 3
<211> LENGTH: 21
<212> TYPE: DNA
<213> ORGANISM: Artificial Sequence
<220> FEATURE:
<223> OTHER INFORMATION: Pax6 forward primer

<400> SEQUENCE: 3
ccagaaagga tgcctcataa a                                            21

<210> SEQ ID NO 4
<211> LENGTH: 18
<212> TYPE: DNA
<213> ORGANISM: Artificial Sequence
<220> FEATURE:
<223> OTHER INFORMATION: Pax6 reverse primer

<400> SEQUENCE: 4
tctgcgcgcc cctagtta                                                18

<210> SEQ ID NO 5
<211> LENGTH: 20
<212> TYPE: DNA
<213> ORGANISM: Artificial Sequence
<220> FEATURE:
```

<223> OTHER INFORMATION: BMP4 forward primer

<400> SEQUENCE: 5
tgagcctttc cagcaagttt                                        20

<210> SEQ ID NO 6
<211> LENGTH: 20
<212> TYPE: DNA
<213> ORGANISM: Artificial Sequence
<220> FEATURE:
<223> OTHER INFORMATION: BMP4 reverse primer

<400> SEQUENCE: 6
gcattcggtt accaggaatc                                        20

<210> SEQ ID NO 7
<211> LENGTH: 20
<212> TYPE: DNA
<213> ORGANISM: Artificial Sequence
<220> FEATURE:
<223> OTHER INFORMATION: Noggin forward primer

<400> SEQUENCE: 7
tcgaacaccc agaccctatc                                        20

<210> SEQ ID NO 8
<211> LENGTH: 20
<212> TYPE: DNA
<213> ORGANISM: Artificial Sequence
<220> FEATURE:
<223> OTHER INFORMATION: Noggin reverse primer

<400> SEQUENCE: 8
catgaagcct gggtcgtagt                                        20

<210> SEQ ID NO 9
<211> LENGTH: 22
<212> TYPE: DNA
<213> ORGANISM: Artificial Sequence
<220> FEATURE:
<223> OTHER INFORMATION: Eomes forward primer

<400> SEQUENCE: 9
aggcgcaaat aacaacaaca cc                                     22

<210> SEQ ID NO 10
<211> LENGTH: 21
<212> TYPE: DNA
<213> ORGANISM: Artificial Sequence
<220> FEATURE:
<223> OTHER INFORMATION: Eomes reverse primer

<400> SEQUENCE: 10
attcaagtcc tccacgccat c                                      21

<210> SEQ ID NO 11
<211> LENGTH: 20
<212> TYPE: DNA
<213> ORGANISM: Artificial Sequence
<220> FEATURE:
<223> OTHER INFORMATION: Brachyury forward primer

<400> SEQUENCE: 11
tgcttccctg agacccagtt                                        20

```
<210> SEQ ID NO 12
<211> LENGTH: 25
<212> TYPE: DNA
<213> ORGANISM: Artificial Sequence
<220> FEATURE:
<223> OTHER INFORMATION: Brachyury reverse primer

<400> SEQUENCE: 12
gatcacttct ttcctttgca tcaag                                         25

<210> SEQ ID NO 13
<211> LENGTH: 18
<212> TYPE: DNA
<213> ORGANISM: Artificial Sequence
<220> FEATURE:
<223> OTHER INFORMATION: FoxA2 forward primer

<400> SEQUENCE: 13
gggagcggtg aagatgga                                                 18

<210> SEQ ID NO 14
<211> LENGTH: 22
<212> TYPE: DNA
<213> ORGANISM: Artificial Sequence
<220> FEATURE:
<223> OTHER INFORMATION: FoxA2 reverse primer

<400> SEQUENCE: 14
tcatgttgct cacggaggag ta                                            22

<210> SEQ ID NO 15
<211> LENGTH: 18
<212> TYPE: DNA
<213> ORGANISM: Artificial Sequence
<220> FEATURE:
<223> OTHER INFORMATION: Sox17 forward primer

<400> SEQUENCE: 15
ggcgcagcag aatccaga                                                 18

<210> SEQ ID NO 16
<211> LENGTH: 18
<212> TYPE: DNA
<213> ORGANISM: Artificial Sequence
<220> FEATURE:
<223> OTHER INFORMATION: Sox17 reverse primer

<400> SEQUENCE: 16
ccacgacttg cccagcat                                                 18

<210> SEQ ID NO 17
<211> LENGTH: 20
<212> TYPE: DNA
<213> ORGANISM: Artificial Sequence
<220> FEATURE:
<223> OTHER INFORMATION: ChAT forward primer

<400> SEQUENCE: 17
tttgtcctct ccactagcca                                               20

<210> SEQ ID NO 18
<211> LENGTH: 20
<212> TYPE: DNA
<213> ORGANISM: Artificial Sequence
<220> FEATURE:
<223> OTHER INFORMATION: ChAT reverse primer
```

<400> SEQUENCE: 18
atacccattt gggaccacag                                              20

<210> SEQ ID NO 19
<211> LENGTH: 17
<212> TYPE: DNA
<213> ORGANISM: Artificial Sequence
<220> FEATURE:
<223> OTHER INFORMATION: Lim3 forward primer

<400> SEQUENCE: 19
gaggcgacct gctgcta                                                 17

<210> SEQ ID NO 20
<211> LENGTH: 20
<212> TYPE: DNA
<213> ORGANISM: Artificial Sequence
<220> FEATURE:
<223> OTHER INFORMATION: Lim3 reverse primer

<400> SEQUENCE: 20
gtccaggatg tgctggtcac                                              20

<210> SEQ ID NO 21
<211> LENGTH: 20
<212> TYPE: DNA
<213> ORGANISM: Artificial Sequence
<220> FEATURE:
<223> OTHER INFORMATION: AADC forward primer

<400> SEQUENCE: 21
aggaagccct ggagagagac                                              20

<210> SEQ ID NO 22
<211> LENGTH: 21
<212> TYPE: DNA
<213> ORGANISM: Artificial Sequence
<220> FEATURE:
<223> OTHER INFORMATION: AADC reverse primer

<400> SEQUENCE: 22
attgtcaaag gagcagcatg t                                            21

<210> SEQ ID NO 23
<211> LENGTH: 20
<212> TYPE: DNA
<213> ORGANISM: Artificial Sequence
<220> FEATURE:
<223> OTHER INFORMATION: SHH forward primer

<400> SEQUENCE: 23
agtttcactc ctggccactg                                              20

<210> SEQ ID NO 24
<211> LENGTH: 20
<212> TYPE: DNA
<213> ORGANISM: Artificial Sequence
<220> FEATURE:
<223> OTHER INFORMATION: SHH reverse primer

<400> SEQUENCE: 24
gatgaagaaa acaccggagc                                              20

<210> SEQ ID NO 25
<211> LENGTH: 20

```
<212> TYPE: DNA
<213> ORGANISM: Artificial Sequence
<220> FEATURE:
<223> OTHER INFORMATION: FGF8 forward primer

<400> SEQUENCE: 25
ctctgcttcc aaaggtgtcc                                              20

<210> SEQ ID NO 26
<211> LENGTH: 18
<212> TYPE: DNA
<213> ORGANISM: Artificial Sequence
<220> FEATURE:
<223> OTHER INFORMATION: FGF8 reverse primer

<400> SEQUENCE: 26
caggtcctgg ccaacaag                                                18

<210> SEQ ID NO 27
<211> LENGTH: 20
<212> TYPE: DNA
<213> ORGANISM: Artificial Sequence
<220> FEATURE:
<223> OTHER INFORMATION: Nurr1 forward primer

<400> SEQUENCE: 27
aactgcactt cggcagagtt                                              20

<210> SEQ ID NO 28
<211> LENGTH: 19
<212> TYPE: DNA
<213> ORGANISM: Artificial Sequence
<220> FEATURE:
<223> OTHER INFORMATION: Nurr1 reverse primer

<400> SEQUENCE: 28
aaaagcaatg gggagtcca                                               19
```